United States Patent [19]

Gillard et al.

[11] Patent Number: 5,225,421

[45] Date of Patent: Jul. 6, 1993

[54] 3-HETERO-SUBSTITUTED-N-BENZYL-INDOLES AND MEDICAL METHODS OF USE THEREFOR

[75] Inventors: John W. Gillard, Baie d'Urfe; Howard E. Morton, Dollard des Ormeaux; Rejean Fortin, Montreal-Nord; Yvan Guindon, Montreal, all of Canada

[73] Assignee: Merck Frosst Canada, Inc., Kirkland, Canada

[21] Appl. No.: 760,443

[22] Filed: Sep. 16, 1991

Related U.S. Application Data

[60] Division of Ser. No. 130,771, Dec. 9, 1987, Pat. No. 5,081,138, which is a continuation-in-part of Ser. No. 942,900, Dec. 17, 1986, abandoned.

[51] Int. Cl.[5] .................. C07D 403/00; C07D 401/12; A61K 31/40
[52] U.S. Cl. ..................................... 514/314; 546/174; 546/176; 546/183; 546/256; 546/273; 546/278; 514/339; 514/345; 514/354
[58] Field of Search ............... 546/176, 174, 183, 256, 546/273, 278; 514/314, 339, 345, 354

[56] References Cited

U.S. PATENT DOCUMENTS 5,081,138 1/1992 Gillard et al. ................ 514/381

OTHER PUBLICATIONS

Tetra. Lett. 24(33), 3531-2 (1983).
C.A. 84(5): 30798t (1976).
C.A. 90(19): 15920j (1979).

*Primary Examiner*—David B. Springer
*Attorney, Agent, or Firm*—Gabriel Lopez; Joseph F. DiPrima

[57] ABSTRACT

Compounds having the formula:

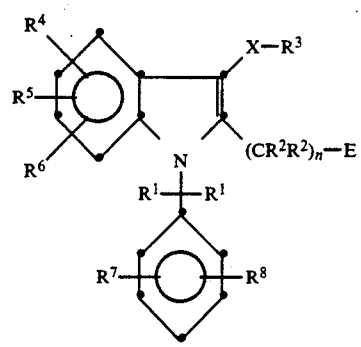

are inhibitors of leukotriene biosynthesis. These compounds are useful as anti asthmatic, anti allergic, anti-inflammatory, and cytoprotective agents. They are also useful in treating diarrhea, hypertension, angina, platelet aggregation, cerebral spasm, premature labor, spontaneous abortion, dysmenorrhea, and migraine.

8 Claims, No Drawings

3-HETERO-SUBSTITUTED-N-BENZYL-INDOLES AND MEDICAL METHODS OF USE THEREFOR

CROSS-REFERENCE

This is a division of Ser. No. 130,771 filed Dec. 9, 1987, now 5,081,138, which is a C-I-P of U.S. Ser. No. 942,900, filed Dec. 17, 1986, abandoned.

BACKGROUND OF THE INVENTION

The leukotrienes and their biological activities, especially their roles in various disease states and conditions have been described. For example, see EP 140,684 (May 8, 1985), which is incorporated herein by reference.

Several classes of compounds exhibit ability to inhibit the biosynthesis of leukotrienes in mammals, especially humans.

See, for example, EP 166,591 (Jan. 2, 1986). The compounds of the present invention are distinguished from those of EP 166,591 in the important feature of possessing a heteroatom at position 3 in place of a hydrogen or carbon substituent. The heteroatom introduces unique electronic and chemical properties into the indole nucleus. The compounds of the present invention are further distinguished in that they uniquely inhibit the biosynthesis of leukotrienes, whereas those of EP 166,591 are antagonists of prostaglandins which also possess leukotriene biosynthesis inhibitory properties.

CH-A 454,858 and CH-A 455,777 teach derivatives of indole 2 acetic acid as useful for the treatment of inflammatory deseases. The compounds of these two Swiss patents are distinguished from those of the present invention by the same chemical differences as in EP 166,591, as well as by differences in the scope of their biological activities.

Walton et al., J. Med. Chem., 11, 1252 (1968) teach certain indole 3 acetic acid derivatives assayed for tumor chemotherapy activity. Walton et al. teach compounds with an alkanoic acid in the 3-position, rather than in the 2-position, and they also lack a heteroatom substituent. The single compound of Walton et al. with a 2-alkanoic acid also lacks a 3-hetero substituent. Walton et al. disclose no useful biological activity for their indole 2-alkanoic acid.

JP-238017 teaches 3 substituted-2-phenylindole derivatives as having lipoxygenase and cyclooxygenase inhibiting activity. In addition to the important differences in biological activities, these compounds possess a phenyl group in the 2-position and are lacking the N-benzyl substituent of the compounds of the present invention.

SUMMARY OF THE INVENTION

The present invention relates to compounds having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to inhibit the pathologic actions of leukotrienes on the cardiovascular and vascular systems for example, actions such as result in angina or endotoxin shock. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemic; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$ and $E_4$ are known to contribute to various disease conditions such as asthma, psoriasis, pain, ulcers and systemic anaphylaxis. Thus inhibition of the synthesis of such compounds will alleviate these and other leukotriene related disease states.

DETAILED DESCRIPTION

The compounds of this invention are best realized by Formula I:

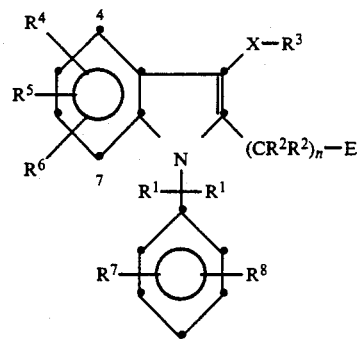

wherein:

$R^1$ is H or loweralkyl;

$R^2$ is H or loweralkyl, or two $R_2$'s may be joined to form a ring of 3-6 atoms;

$R^3$ is alkyl, $C_2$-$C_6$ alkenyl, substituted or unsubstituted phenyl, —$(CH_2)_m$—Het, or M-substituted alkyl;

$R^4$, $R^5$ and $R^6$ is each independently H, loweralkyl, $C_2$-$C_6$ alkenyl, or —$(CR^2R^2)_pM$;

$R^7$ and $R^8$ are independently H, $C_1$-$C_3$ alkyl, halogen, OH, CN, $CF_3$, $C_1$-$C_3$ alkoxy, $C_1$-$C_3$ alkylthio, $CO_2H$, $C_1$-$C_3$ alkoxycarbonyl, $C_1$-$C_3$ alkylcarbonyl, or azide;

$R_9$ is $CF_3$, loweralkyl, substituted or unsubstituted benzyl, or substituted or unsubstituted phenyl;

$R^{10}$ is H, loweralkyl, unsubstituted phenyl, unsubstituted benzyl, or two $R^{10}$'s attached to a nitrogen may form a ring of 5 to 7 members;

$R^{11}$ is H or —$(CH_2)_qR^9$;

$R^{12}$ is loweralkyl substituted or unsubstituted benzyl, or substituted or unsubstituted phenyl;

$R^{13}$ is H, loweralkyl, substituted or unsubstituted phenyl, or substituted or unsubstituted benzyl;

$R^{14}$ is —$CH_2CH_2N(R^{10})_2$, $CH_2CH(OH)CH_2OH$, —$CH_2O_2CC(CH_3)_3$, —$CH(CH_3)O_2CC(CH_3)_3$,

[Structural formulas shown:]

—CH₂N(succinimide), —CH(CH₃)—N(succinimide),

—CH₂CH₂NHC(O)—(pyridyl)—, —CH(C₂H₅)—N(phthalimide),

—(CH₂)₂N(succinimide), —(CH₂)₂N(phthalimide),

—(CH₂)₂NHAc, —CH₂—N(glutarimide), —CH₂—CH=N—N(CH₃) (imidazole),

—CH₂—N(acetyl, N-methyl), —CH₂—C(CH₃)=CH—O—C(O)CH₃ (or similar),

—CH(CH₃)—N(N-methylpiperazine-2,5-dione), or —CH₂—N(2-pyrrolidinone);

E is CH₂OH, CO₂R¹³, CO₂R¹⁴, tetrazol-5-yl, CHO, C(O)NR²R², C(O)NHS(O)₂R⁹, or C(O)N(OR²)R²;

M is a) OR¹⁰;
b) halogen;
c) CF₃;
d) SR⁹;
e) substituted or unsubstituted phenyl;
f) COOR¹⁰;

g) $\overset{O}{\overset{\|}{C}}$—R¹¹;

h) tetrazole;

i) —NH—$\overset{O}{\overset{\|}{C}}$—R¹¹;

j) —NR¹⁰R¹⁰;
k) —NHSO₂R⁹;

l) —$\overset{O}{\overset{\|}{C}}$—CH₂OH;

m) —S(O)R⁹;
n) —CONR¹⁰R¹⁰;
o) —S(O)₂NR¹⁰R¹⁰;
p) —S(O)₂R⁹;
q) NO₂;

r) O—$\overset{O}{\overset{\|}{C}}$—R¹¹;

s) O—$\overset{O}{\overset{\|}{C}}$—NR¹⁰R¹⁰;

t) O—$\overset{O}{\overset{\|}{C}}$—OR¹²;

u) CN;
v) N₃; or
w) H;
X is O, S, S(O), or S(O)₂;
m is 0–2;
n is 0–5
p is 0–3; and
q is 0–4;
and the pharmaceutically acceptable salts thereof.

Alkyl and alkenyl are intended to include linear, branched, cyclic, and linear/cyclic (e.g., alkylcycloalkyl) structures.

As used herein, the term "alkyl" includes "loweralkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-ethyl-2,2-methyl-4-propylnonyl, cyclododecyl, adamantyl and the like.

As used herein, the term "loweralkyl" includes those alkyl groups of from 1 to 7 carbon atoms. Examples of loweralkyl fragments include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, and the like.

Alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl and the like.

As used herein, the term "alkoxy" includes those alkoxy groups of from 1 to 7 carbon atoms of either a straight, branched, or cyclic configuration. Examples of alkoxy fragments include methoxy, ethoxy, propoxy, isopropoxy, cyclopropyloxy, pentyloxy, cycloheptyloxy, and the like.

Substituted phenyl and substituted benzyl include 1 or 2 substituents on the benzene ring selected from C₁-C₃ alkyl, halogen, CN, CF₃, C₁-C₃ alkoxy, C₁-C₃ alkylthio, CO₂H, C₁-C₃ alkoxycarbonyl, C₁-C₃ alkylcarbonyl and azide.

By "Het" is meant 2, 3, or 4 pyridyl; tetrazolyl; 2- or 3-thienyl; 2-, 4-, or 5-thiazolyl; 2-, 4-, or 5-thiazolinyl; 1, 2, 4-, or 5 imidazolyl; 3-[1,2,5]-thiadiazolyl; benzothiazol 2 yl; or 2-, 3-, or 4-quinolinyl, each optionally substituted with 1 or 2 substituents selected from C₁-C₃ alkyl, halogen, CN, CF₃, C₁-C₃ alkoxy, C₁-C₃ alkylthio, CO₂H, C₁-C₃ alkoxycarbonyl, C₁-C₃ alkylcarbonyl and azide.

By "halogen" is meant F, Cl, Br, and I.

It is intended that the definitions of any substituent (e.g., $R^2$, $R^4$, $R^5$, etc.) in a particular molecule be independent of its definitions elsewhere in the molecule. Thus, $-NR^2R^2$ represents $-NHH$, $-NHCH_3$, $-NCH_3CH_3$, etc.

Some of the compounds described herein contain one or more centers of asymmetry and may thus give rise to diastereoisomers and optical isomers. The present invention is meant to comprehend such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z geometric isomers.

Preferred compounds of Formula I are represented by Formula Ia:

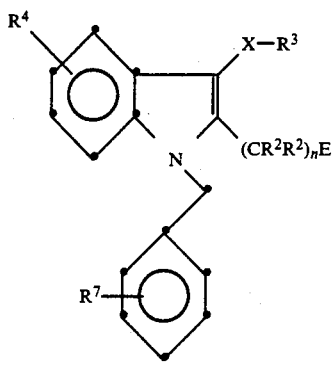

wherein:

$R^3$ is loweralkyl (preferably branched loweralkyl), alkylcycloalkyl, alkyl-substituted phenyl, unsubstituted phenyl, or unsubstituted benzyl;

$R^4$ is loweralkyl (preferably branched loweralkyl), halo, substituted or unsubstituted phenyl, or alkoxy;

$R^7$ is alkyl, alkoxy, azide, halogen, or hydroxy;

$R^{13}$ is H or loweralkyl;

E is $CO_2R^{13}$, $CONH_2$, or tetrazol-5-yl;

n is 1-3;

and the remaining substituents are as defined for Formula I.

It will be understood that in the discussion of methods of treatment which follows, references to the compounds of Formula I are meant to also include the pharmaceutically acceptable salts.

The ability of the compounds of Formula I to inhibit biosynthesis of the leukotrienes makes them useful for inhibiting the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such as arthritis or inflammatory bowel disease, 4) pain, 5) skin conditions such as psoriasis and the like, and 6) cardiovascular conditions such as angina, endotoxin shock, and the like, and that the compounds are cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

Compounds of Formula I can be tested using the following assays to determine their mammalian leukotriene biosynthesis inhibiting activity.

Rat Peritoneal Polymorphonuclear (PMN) Leukocyte Assay

Rats under ether anesthesia are injected (i.p.) with 8 ml of a suspension of sodium caseinate (6 grams in ca. 50 ml water). After 15-24 hr. the rats are sacrificed ($CO_2$) and the cells from the peritoneal cavity are recovered by lavage with 20 ml of buffer (Eagles MEM containing 30 mM HEPES adjusted to pH 7.4 with NaOH). The cells are pelleted (350×g, 5 min.), resuspended in buffer with vigorous shaking, filtered, through lens paper, recentrifuged and finally suspended in buffer at a concentration of 10 cells/ml. A 500 μl aliquot of PMN suspension and test compound are preincubated for 2 minutes at 37° C., followed by the addition of 10 μM A-23187. The suspension is stirred for an additional 4 minutes then bioassayed for $LTB_4$ content by adding an aliquot to a second 500 μl portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Mouse Macrophage Assay

Mouse peritoneal macrophages are treated sequentially with arachidonic acid (labelled with tritium); the compound being evaluated as an inhibitor, and a stimulator (zymosan). Metabolites derived from arachidonic acid ($PGE_2$, 6 keto $PG-F_{1a}$ and leukotriene $C_4$) are separated from the incubation medium by extraction and chromatography, and then quantitated by determining the amount of radioactivity (cpm) associated with each of them. Inhibitors cause a reduction in the amount of radioactivity (cpm) associated with a given metabolite. (This protocol is identical to that described in the reference except that the radioactivity herein associated with the $LTC_4$ is determined by counting an aliquot of the final aqueous solution directly rather than chromatographing it first.

Reference: Humes, J. L. et al., *J. Biol. Chem.*, 257, 1591-4, (1982).

Antigen Challenge 'in vitro' Assay

Male guinea pigs weighing 300-350 g are sensitized by injecting (intraperitoneally) 0.5 ml of a suspension containing 0.4 mg of egg albumin (Ovalbumin, Grade V, Sigma Chemical Co.) and 4.0 q aluminum hydroxide in 19.6 ml of saline. Two weeks are permitted for sensitization to occur.

Three sensitized guinea pigs are stunned and exanguinated. The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No.7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified Krebs-Henseleit buffer solution gassed with 95% $O_2$ and 5% $CO_2$ at 37° C. Two different methods are used to test experimental compounds.

$^1$modified Krebs solution in grams/liter and (mM): NaCl 6.87 (120); glucose 2.1 (11); NaHCO$_3$ 2.1 (25); KCl - 0.32 (4.72); CaCl$_2$ - 0.28 (2.5); MgSO$_4$.7H$_2$O - 0.11 (0.5); KH$_2$PO$_4$ - 0.16 (1.2); pH at bathing solution =7.35±0.05.

Protocol A

Mepyramine (0.55 μg/ml) and indomethacin (2.67 μq/ml) are added to the buffer to avoid the contribution of histamine receptors and cyclooxygenase products to the contraction. To record responses one end of the tracheal chain is attached to a Gould Statham UC 2 force displacement transducer which is connected to a Beckman Type R dynograph. The preparations are allowed to equilibrate for one hour during which time the tissues are automatically washed (10 ml volume displacement) every 6 minutes.

After the equilibration period the tissues are primed with methacholine (3 μg/ml; $1.5 \times 10^5$M), washed and allowed to recover to baseline. The tissues are treated again with a second dose of methacholine, washed, allowed to return to baseline and washed for an additional hour.

Two chains are used as a control. These are incubated in a concentration of egg albumin sufficient to induce an average contraction of 50–80% of the methacholine response.

Each compound to be tested is added to a bath (at a final concentration of 10 μg/ml) 15 minutes prior to challenging the fresh chains with egg albumin.

The response of the challenged tissue is expressed as a percentage of the methacholine maximum. The percentage inhibition for each compound is then calculated. Compounds which at 10 μg/ml (final concentration) inhibit the egg albumin response by 50% or more are retested at a lower concentration.

Protocol B

Tracheal chains are prepared as described above. Experiments are carried out on tonal (no indomethacin) or non-tonal (0.5 mg/mL indomethacin) preparations in the presence of $1 \times 10^{-7}$M atropine and/or 2.0 mg/mL mepyramine. The effects of various compounds alone or in combination (30 minutes pretreatment) or drug vehicle (DMSO or H$_2$O) are determined against a standared single dose challenge to 0.1 mg/mL ovalbumin. The responses are expressed as a percent of the maximal contraction that could be produced by histamine (10 mg/mL) before addition of the various compounds. Peak percent maximal contractile responses to antigen are recorded at various time intervals (0–60 min) after addition of antigen to control and compound-treated tissues.

For non-tonal experiments, indomethacin is added to the Krebs' buffer at the beginning of the experiment so that the tissues are continuously bathed with this drug throughout the experiment. All tissues are primed 2–3 times with a maximal concentration of histamine (10 mg/mL) and responses to antigen are expressed at a percent of the maximum contraction to histamine.

In the absence of indomethacin (tonal), the tissues spontaneously develop intrinsic tone following the initial priming procedure with histamine (10 mg/mL) and isoproterenol (0.5 mg/mL) which are administered to determine maximum contraction and relaxation, respectively. If the compound tested in the absence of indomethacin (tonal preparation) decreases intrinsic tracheal tone, this alteration in baseline tone is taken into account and responses to antigen challenge are expressed as a percent of the new histamine maximum (histamine response plus the decrease in baseline tone).

Asthmatic Rat Assay

Rats are obtained from an inbred line of asthmatic rats. Both female and male rats from 200 to 300 g are used.

Egg albumin (EA), grade V, crystallized and lyophilized, is obtained from Sigma Chemical Co., St. Louis. Bordetella pertussis vaccine, containing $30 \times 9^9$ killed bacteria per ml is obtained from the Institute Armand-Frappier, Laval des Rapides, Quebec. Aluminum hydroxide is obtained from the Regis Chemical Company, Chicago.

The challenge and subsequent respiratory recordings are carried out in a clear plastic box with internal dimensions $10 \times 6 \times 4$ inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 ml of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 ml of a suspension containing 1 mg EA and 200 mg aluminum hydroxide in saline. Simultaneously, they receive an injection (intraperitoneally) of 0.5 ml of B. pertussis vaccine. They are used between days 14 and 18 postsensitization. In order to eliminate the serotonin component of the response, rats are pretreated intravenously 5 minutes prior to aerosol challenge with 30 μm/kg methylserzide. Rats are then exposed to an aerosol of 3% EA in saline for exactly 1 minute, then their respiratory profiles are recorded for a further 25 to 30 minutes. The duration of continuous dyspnoea is measured from the respiratory recordings.

Compounds are generally administered either intraperitoneally 1 hour prior to challenge or orally 1 and ½ hours prior to challenge. They are either dissolved in dimethylsulfoxide or suspended in 0.1% methocel and 0.5% Tween 80. The volume injected is 2 ml/kg (intraperitoneally) or 10 ml/kg (orally). Prior to oral treatment rats are starved overnight. Their activity is determined in terms of their ability to decrease the duration of symptoms of dyspnoea in comparison with a group of vehicle-treated controls. Usually, a compound is evaluated at a series of doses and an $ED_{50}$ is determined. This is defined as the dose (mg/kg) which would inhibit the duration of symptoms by 50%.

PAF-Induced Hyperalgesia Assay

Female Sprague-Dawley rats, 35 to 40 q are fasted overnight. Platelet activating factor, PAF, (L-lecithin B-acetyl O-alkyl) 1 µg/0.1 ml is given by subplantar injection in the rat paw. The compounds to be evaluated are homogenized in Aqueous Vehicle (0.9% benzyl alcohol, 0.5% Tween 80 and 0.4% methylcellulose) and administered orally in a volume of 0.1 ml, 30 minutes prior to PAF.

Animals are tested 1, 2, 3 and 4 hours after PAF administration. The vocalization threshold, defined as the pressure (mmHg) needed to evoke a squeak response, was recorded for both the injected and contralateral paw. No animal is subjected to pressure greater than 60 mmHg. Hyperalgesia is defined as a decrease in vocalization threshold as compared to a normal paw. Percent inhibition of hyperalgesia is calculated as the proportion of animals with vocalization thresholds greater than 200% of controls.

Brewer's Yeast Hyperalgesia Assay

The standard method [Winter, C. A. et al., *J. Pharm. Exp. Ther.* 150, 165-171 (1965)] for yeast hyperalgesia is used. Female Sprague Dawley rates, 35-40 g are fasted overnight. A 5% solution (volume 0.1 ml) of Brewer's yeast is injected into the rat paw. The compound is homogenized in aqueous vehicle and given orally 2 hours after yeast. Vocalization thresholds are recorded 1 hour after drug (3 hours after yeast). Percent inhibition of hyperalgesia is determined by the proportion of animals with vocalization thresholds greater than 25 mmHg.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti asthmatic, anti allergic or anti inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co administration of a compound of the Formula I with a non steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans, will generally range from about 0.1 mg/kg to about 100 mg/kg, preferably from about 1 mg/kg to about 100 mg/kg. The dosage may be administered in single or divided individual doses.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non toxic bases or acids including inorganic bases or acids and organic bases or acids.

Salts derived from inorganic bases include aluminum, ammonium, calcium, copper, ferric, ferrous, lithium, magnesium, manganic, manganous, potassium, sodium, zinc salts and the like. Particularly preferred are the ammonium, calcium, magnesium, potassium, and sodium salts. Salts derived from pharmaceutically acceptable organic non toxic bases include salts of primary, secondary, and tertiary amines, substituted amines including naturally occurring substituted amines, cyclic amines and basic ion exchange resins, such as arginine, betaine, caffeine, choline, $N,N^1$- dibenzylethylenediamine, diethylamine, 2-diethylaminoethanol, 2-dimethylaminoethanol, ethanolamine, ethylenediamine, N-ethyl morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Particularly preferred are hydrobromic, hydrochloric, phosphoric, and sulfuric acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

Dosage forms include tablets, troches, dispersions, suspensions, solutions, capsules, creams, ointments, aerosols, and the like.

For use where a composition for intravenous administration is employed, a suitable dosage range for anti-asthmatic, anti-inflammatory or anti-allergic use is from about 0.001 mg to about 10 mg (preferably from about 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebuliser, or as a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of Compound I include transdermal devices, aerosols, creams, ointments, lotions, dusting powders, and the like.

For the treatment of diseases of the eye, ophthalmic preparations for ocular administration comprising 0.001-1% by weight solutions or suspensions of the compounds of Formula I in an acceptable ophthalmic formulation may be used.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non aqueous liquid, an oil in water emulsion or a water in-oil liquid emulsion.

Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding. optionally with one or more accessory ingredients. Compressed tablets may be prepared by compressing in a suitable machine, the active ingredient in a free flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |
| Tablet | mg/tablet |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and (5) the oxicams
or a pharmaceutically acceptable salt thereof. NSAIDs which are within the scope of this invention are those disclosed in EP 140,684.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 5, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in European Patent Application Nos. 56,172 (Jul. 21, 1982) and 61,800 (Oct. 6, 1982); and in U.K. Patent Specification No. 2,058,785, which are hereby incorporated herein by reference.

Pharmaceutical compositions comprising the Formula I compounds may also contain as the second active ingredient prostaglandin (including thromboxane) antagonists such as those disclosed in EP 11,067 (May 28, 1980), EP 166,591 (Jan. 1, 1986), or in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Another useful pharmaceutical composition comprises the Formula I compounds in combination with serotonin antagonists such as methysergide, the serotonin antagonists disclosed in Nature, vol. 316, pages 126–131, 1985, and the like. Each of the references referred to in this paragraph is hereby incorporated herein by reference.

When the second active ingredient in compositions of this invention is a thromboxane synthetase inhibitor, such inhibitor can be as described in UK 2,038,821 (e.g., UK 37248 and dazoxiben hydrochloride), U.S. Pat. No. 4,217,357 (e.g., UK 34787), U.S. Pat. No. 4,444,775 (e.g., CGS 13080), U.S. Pat. No. 4,226,878 (e.g., ONO 046), U.S. Pat. No. 4,495,357 (e.g., U63557A) U.S. Pat. No. 4,273,782 (e.g., UK 38485), or EP 98,690 (e.g., CV 4151).

The combination compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration. These compositions are formulated similarly to the compositions discussed above.

It will be understood, however, that the specific dose level for any particular patient will depend upon a variety of factors including the activity of the specific compound employed, the age, body weight, general health, sex, diet, time of administration, route of administration, rate of excretion, dug combination and the severity of the particular disease undergoing therapy.

Compounds of the present invention can be prepared according to the following methods.

METHOD A—From Non-indole Precursors a) Fischer Cyclization

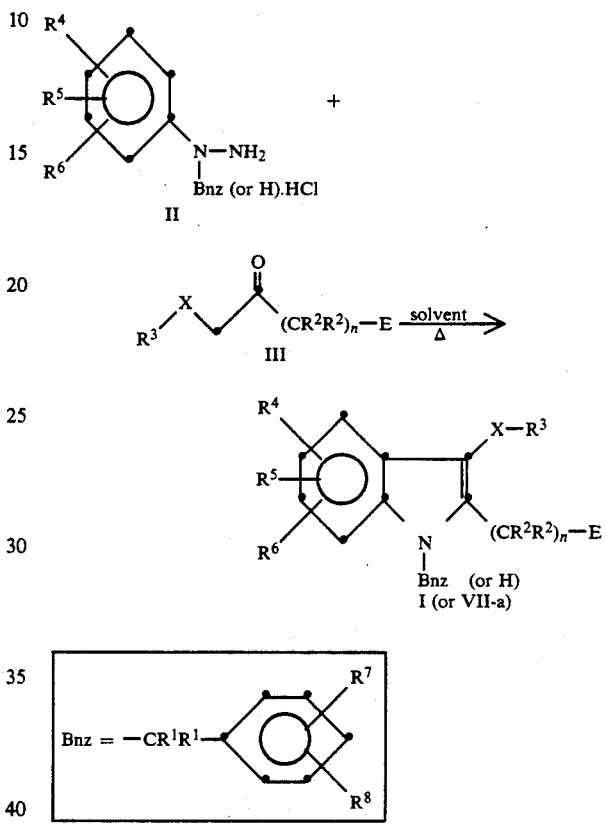

These compounds (E=$CO_2R^{13}$, $CH_2OH$, $CONR^2R^2$, $CONHSO_2R^9$) are prepared utilizing standard Fischer Indole conditions. (See, for example, the review of "Heterocyclic Compounds", 25, Parts I, II, and III, W. J. Houlihan, ed., Interscience, John Wiley & Sons, New York, 1979.)

Thus, treatment of the hydrazine II with the α-heteroketone III in an alcoholic solvent at a temperature between 20° C. and the refluxing temperature of the solvent yields I. Illustrative of such alcoholic solvents are: methanol, ethanol, isopropanol, tert-butanol, tert-amylalcohol and the like.

Where the substituent on the hydrazine nitrogen is H, this method yields compounds of the formula VII-a.

b) Via N-chloroanilines

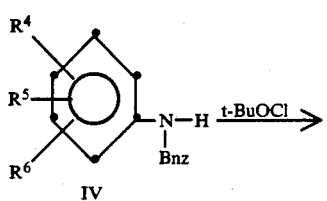

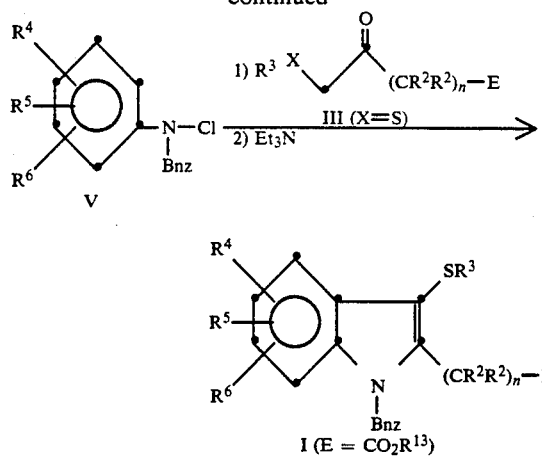

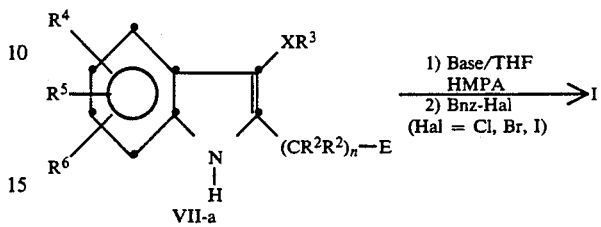

The N-chloroaniline V is formed in situ using t-butyl hypochlorite or some other chlorinating source. (See, P. G. Gassman and T. J. van Bergen, J. Amer. Chem, Soc., 95 590 (1973)). Reaction of V with the thioketone III at low temperature ($-78°$ C.$\rightarrow -23°$ C.) and subsequent treatment with a trialkylamine base (such as triethylamine, diisopropylethylamine, etc.) affords the 3-thioindole I.

METHOD B—From Indole Precursors a) Metalated Enamines

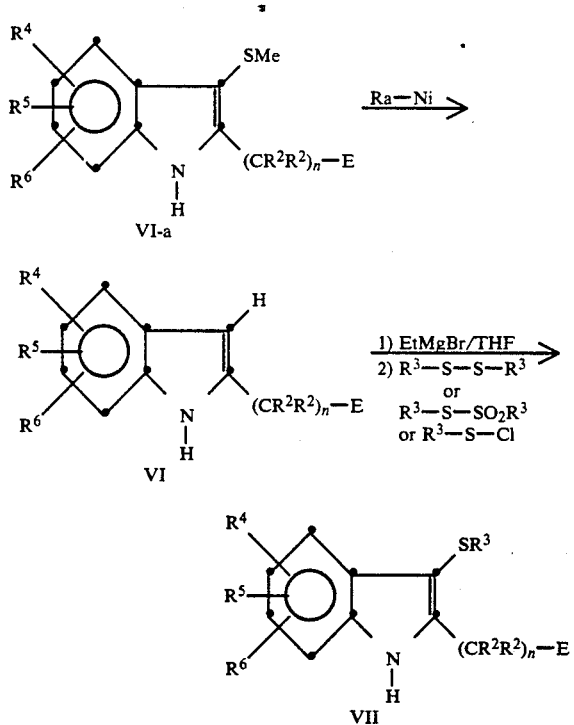

Using the Procedure of Method A, compounds VI-a (which are representatives of VII-a) are prepared, which can then be desulfurized with Raney nickel to yield indoles VI.

Deprotonation of indoles of the type VI at the nitrogen atom using a strong base (EtMgBr, MeMgBr, butyllithium, lithium diisopropylamide, potassium hexamethyldisilamide, etc.) and reaction of the resultant salt with the appropriate thiolating reagent affords the 3-thioindole VII. Use of the reagent R3SCl often proceeds spontaneously and a weak base such as triethylamine is necessary only to neutralize the HCl formed.

b) Alkylation at Nitrogen

Deprotonation of compound VII-a (from Method A) with base (lithium diisopropylamide, potassium hexamethyldisilamide, ethyl magnesium bromide, potassium hydride, etc.) and reaction of the resultant anion with a benzyl halide or substituted benzyl halide gives I.

Sulfenylation of N-Benzylindoles

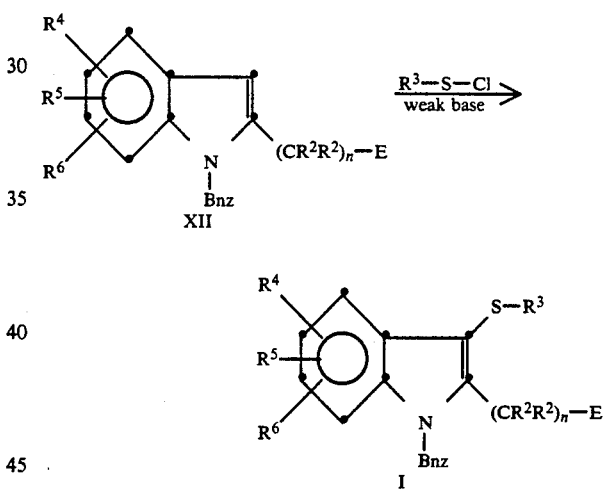

Alternatively, sulfide derivatives of I can be prepared by the action of 0° C. to reflux temperatures of substituted sulfenyl halides in the presence of a weak base of N-benzylindole derivative XII in solvent (such as methylene chloride or chloroform, 1,2-dichloroethane).

METHOD C—Functional Group Manipulations a) Preparation of Sulfoxides and Sulfones

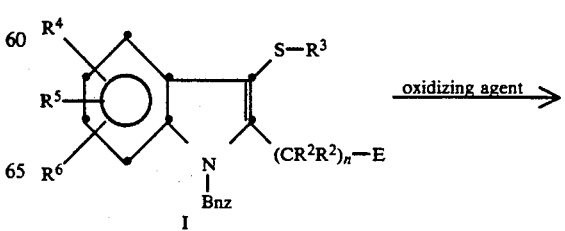

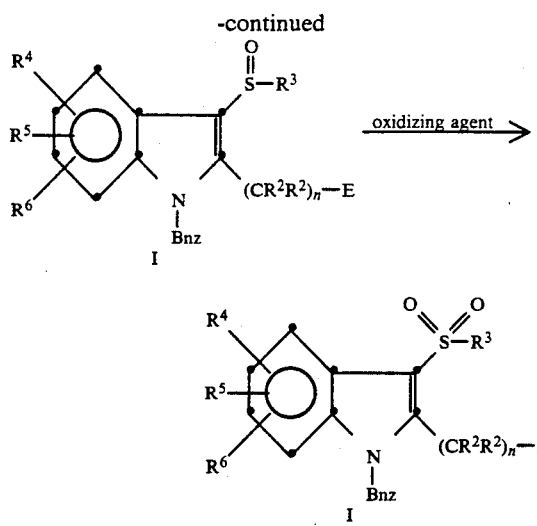

Sulfoxide and sulfone derivatives of I can be prepared by using known oxidizing agents such as meta-chloroperbenzoic acid (m-CPBA), hydrogen peroxide, peracetic acid, oxone and the like, on a sulfoxide or sulfide precursor as illustrated in Method C(a). In a similar way, sulfoxide and sulfone derivatives of intermediates such as VII can be prepared. Either limiting the amount of oxidizing agent or monitoring the course of the reaction allows isolation of the sulfoxides.

b) Alkylation at Carbon

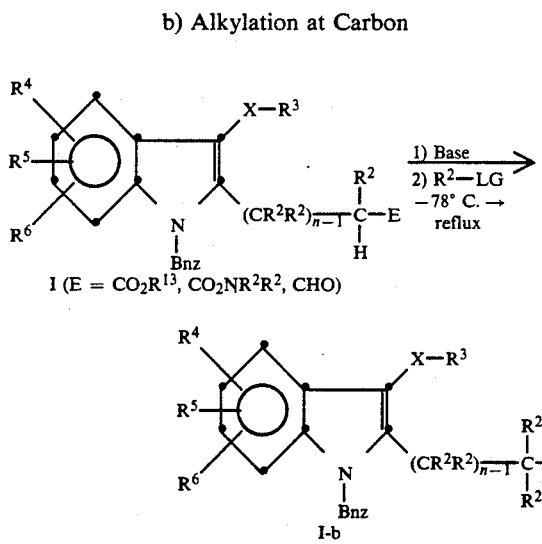

Deprotonation at the carbon α to the E group can be carried out utilizing a strong base such as lithium or potassium diisopropylamide (or potassium hexamethyldisilamide or KH) in an inert solvent (e.g., tetrahydrofuran, ether, toluene, or mixtures thereof) at temperatures from −78° C. to 0° C. Reaction of the resultant enolate with an alkylating reagent ($R^2$−LG; LG=Cl, Br, I, O-tosyl, O-mesyl; $R^2$ is loweralkyl) at from −78° C. to the reflux temperature of the solvent gives the corresponding alkylated compounds I-b.

c) Oxidation and Reduction of E

I $\longrightarrow$ I-c

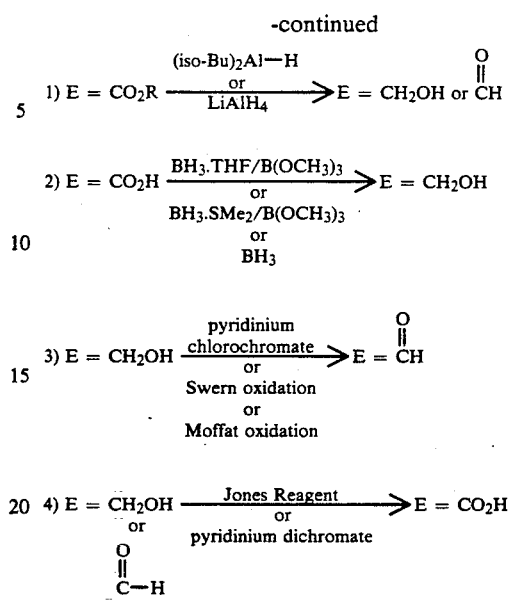

Oxidized or reduced derivatives (I-c) of I may be prepared by the above sequences.

d) Preparation of Amides & Tetrazoles

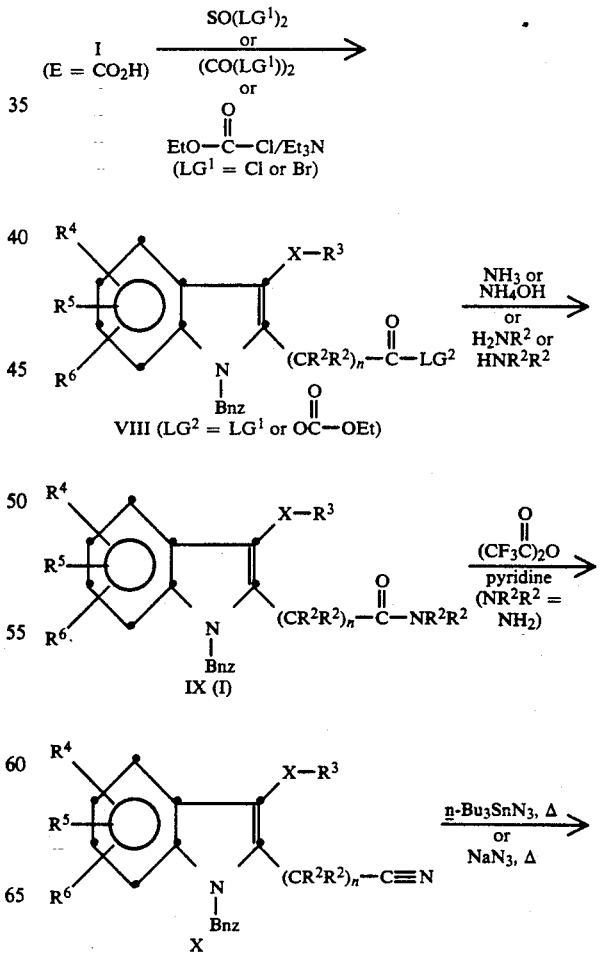

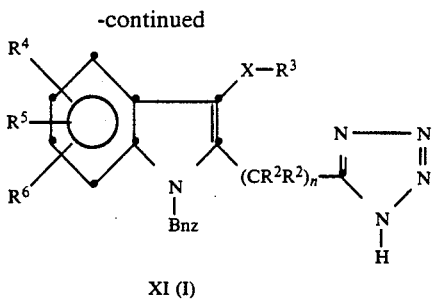

XI (I)

Formation of the activated carboxylic acid derivative VIII and reaction with ammonia gives the amide IX. This material can be dehydrated to give the nitrile X which in turn affords the tetrazole XI on treatment with various sources of azide. Both IX and XI are representatives of structure I.

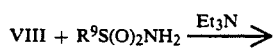

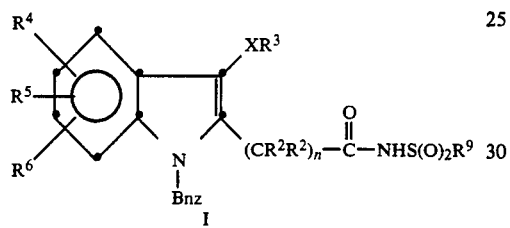

I

Reaction of VIII with sulfonamide derivative XIII in the presence of a weak base such as triethylamine affords the acylsulfonamide compounds of I.

It is deemed to be within the skill of those in the art to protect certain functional groups when employing these methods, as by the use of suitable blocking groups. It is also deemed to be within the skill of those in the art to convert certain functionalities to others at various stages of these methods by standard transformations such as hydrolysis, esterification, oxidation, reduction, and the like.

Referring to Methods A and B above, useful benzyl halides (Bnz-hal, where $R^1=R^1=H$) are shown in Table 2:

TABLE 2

| Compound No. | Hal | $R^7$ | $R^8$ | Compound Name |
|---|---|---|---|---|
| 1. | Cl | 4-Cl | H | 4-chlorobenzyl chloride (Aldrich Chem. Co.) |
| 2. | Cl | 4-OMe | H | 4-methoxybenzyl chloride (Aldrich) |
| 3. | Cl | 2-Cl | 4-Cl | 2,4-dichlorobenzyl chloride (Aldrich) |
| 4. | Br | 2-Cl | H | 2-chlorobenzyl bromide (Aldrich) |
| 5. | Br | 3-Cl | H | 3-chlorobenzyl bromide (Aldrich) |
| 6. | 4-F | 3-Cl | H | 4-fluorobenzyl bromide (Aldrich) |
| 7. | Br | 4-CF$_3$ | H | 4-trifluoromethylbenzyl bromide (Aldrich) |
| 8. | Cl | 4-CO$_2$Me | H | 4-carbomethoxybenzyl chloride (Journ. Amer. Chem. Soc., 1950, 72, 5152) |
| 9. | Cl | 4-SMe | H | 4-methylthiobenzyl chloride (Chem. Abstr. 56:4773 (1962) |
| 10. | Cl | 4-S(O)Me | H | 4-methylsulfinylbenzyl chloride (C.A.:84:105277h (1976)) |
| 11. | Cl | 4-S(O)$_2$Me | H | 4-methylsulfonylbenzyl chloride (C.A.:78:111325 q (1973)) |
| 12. | Br | 4-NO$_2$ | H | 4-nitrobenzyl bromide (Aldrich) |
| 13. | Cl | 4-CONMe$_2$ | H | 4-dimethylcarboxamidobenzyl chloride |
| 14. | Cl | 4-S(O)$_2$NMe$_2$ | H | 4-dimthylsulfamoylbenzyl chloride (C.A. 84:135484r (1976)) |
| 15. | Cl | 4-CO$_2$H | H | 4-carboxybenzyl chloride (Aldrich) |
| 16. | Cl | 4-COMe | H | 4-acetylbenzyl chloride (C.A.:93:230004: (1980)) |

Other 1-benzyl phenylhydrazines of Formula II prepared by the methods of Preparations 1 and 2, are shown in Table 3.

TABLE 3

1-Benzyl Phenylhydrazines

| Compound No. | $R^4,R^5,R^6$ | $R^7,R^8$ | $R^1,R^1$ | Compound Name |
|---|---|---|---|---|
| 1. | 2-Me,H,H | 4-Cl,H | H,H | 1-(4-chlorobenzyl)-1-(2-methylphenyl)hydrazine hydrochloride |
| 2. | 3-F,H,H | 4-Cl,H | H,H | 1-(4-chlorobenzyl)-1-(3-fluorophenyl)hydrazine hydrochloride |
| 3. | 2,4-Cl$_2$,H | 4-Cl,H | H,H | 1-(4-chlorobenzyl)-1-(2,4-dichlorophenyl)-hydrazine hydrochloride |
| 4. | 4-F,H,H | H,H | H,H | 1-(benzyl-1-(4-fluorophenyl)hydrazine hydrochloride |
| 5. | 4-F,H,H | 4-OMe,H | H,H | 1-(4-methoxybenzyl)-1-(4-fluorophenyl)-hydrazine hydrochloride |
| 6. | 4-F,H,H | 3,4-Cl$_2$ | H,H | 1-(3,4-dichlorobenzyl)-1-(4-fluoro-phenyl)-hydrazine hydrochloride |
| 7. | 4-F,H,H | H,H | CH$_3$,H | 1-[1-(phenyl)ethyl]-1-(4-fluorophenyl)-hydrazine hydrochloride |
| 8. | 2-F,H,H | 4-Cl,H | H,H | 1-(4-chlorobenzyl)-1-(2-fluorophenyl)-hydrazine hydrochloride |
| 9. | 4-CF$_3$,H,H | 4-Cl,H | H,H | 1-(4-chlorobenzyl)-1-(4-trifluoromethyl-phenyl)hydrazine hydrochloride |
| 10. | 4-SMe,H,H | 4-Cl,H | H,H | 1-(4-chlorobenzyl-1-(4-methylthiophenyl)-hydrazine hydrochloride |
| 11. | 2-CH(Me)$_2$, | 4-Cl,H | H,H | 1-(4-chlorobenzyl)-1-(2-isopropylphenyl)-hydrazine hydrochloride |

The following abbreviations have the indicated meanings:
Me=methyl
Bz=benzyl
Ph=phenyl
t-Bu=tert-butyl
i-Pr=isopropyl
c-C$_6$H$_{11}$=cyclohexyl
c-Pr=cyclopropyl
c-=cyclo
Ac=acetyl
Tz=5-tetrazolyl The following compounds (Table 1) are within the scope of the invention:

TABLE 1

Novel 3-Hetero-substituted-N-benzyl-indoles

| Ex. | Bnz | R³ | R⁴ | R⁵ | R⁶ | —(CR²R²)ₙ— | E | X |
|---|---|---|---|---|---|---|---|---|
| 1. | 4-Cl-Bz | Ph | 5-Cl | H | H | n = 0 | CO₂Et | S |
| 2. | 4-Cl-Bz | Ph | 5-Cl | H | H | n = 0 | CO₂H | S |
| 3. | 4-Cl-Bz | Me | 5-F | H | H | CH₂ | CO₂Et | S |
| 4. | 4-Cl-Bz | Me | 5-F | H | H | CH₂ | CO₂H | S |
| 5. | 4-Cl-Bz | Me | 5-F | H | H | CH₂ | CO₂H | SO₂ |
| 6. | 4-Cl-Bz | Me | 5-F | H | H | CH(CH₃) | CO₂H | S |
| 7. | 4-Cl-Bz | Ph | 5-F | H | H | C(CH₃)₂ | CO₂H | S |
| 8. | 4-Cl-Bz | Ph | 5-F | H | H | CH₂ | CO₂H | S |
| 9. | 4-Cl-Bz | Ph | 5-F | H | H | CH(CH₃) | CO₂H | S |
| 10. | 4-Cl-Bz | Ph | 5-i-Pr | H | H | CH(CH₃) | CO₂H | S |
| 11. | 4-Cl-Bz | Ph | 5-t-Bu | H | H | CH₂ | CO₂H | S |
| 12. | 4-Cl-Bz | Ph | 5-t-Bu | H | H | CH₂ | CO₂H | SO |
| 13. | 4-Cl-Bz | Ph | 5-t-Bu | H | H | CH₂ | CO₂H | SO₂ |
| 14. | 4-Cl-Bz | Ph | 5-F | H | H | CH₂ | CO₂H | SO₂ |
| 15. | 4-Cl-Bz | Ph | 5-i-Pr | H | H | (CH₂)₂ | CO₂H | S |
| 16. | 4-Cl-Bz | Me | 5-F | H | H | (CH₂)₂ | CO₂H | S |
| 17. | 4-Cl-Bz | Ph | 5-F | H | H | (CH₂)₂ | CO₂H | S |
| 18. | 4-Cl-Bz | Ph | 5-i-Pr | H | H | CH₂C(CH₃)₂ | CO₂H | S |
| 19. | 4-Cl-Bz | Ph | 5-i-Pr | H | H | CH₂C(CH₃)₂ | CO₂H | S |
| 20. | 4-Cl-Bz | Ph | 5-i-Pr | H | H | CH₂C(CH₃)₂ | CO₂H | SO |
| 21. | 4-Cl-Bz | Ph | 5-i-Pr | H | H | CH₂C(CH₃)₂ | CO₂H | SO₂ |
| 22. | 4-Cl-Bz | Ph | 5-Ph | H | H | CH₂C(CH₃)₂ | CO₂H | S |
| 23. | 4-Cl-Bz | Me | 5-F | H | H | CH₂C(CH₃)₂ | CO₂H | S |
| 24. | 4-Cl-Bz | t-Bu | 5-i-Pr | H | H | CH₂C(CH₃)₂ | CO₂H | S |
| 25. | 4-Cl-Bz | t-Bu | 5-i-Pr | H | H | CH₂C(CH₃)₂ | CO₂H | SO |
| 26. | 4-Cl-Bz | t-Bu | 5-i-Pr | H | H | CH₂C(CH₃)₂ | CO₂H | SO₂ |
| 27. | 4-Cl-Bz | t-Bu | 5-i-Pr | H | H | CH₂C(CH₃)₂ | CO₂H | SO₂ |
| 28. | 4-Cl-Bz | Ph | 5-Ph | H | H | (CH₂)₂C(CH₃)₂ | CO₂H | S |
| 29. | 4-Cl-Bz | Ph | 5-i-Pr | H | H | CH₂C(CH₃)₂ | CO₂H | S |
| 30. | 4-Cl-Bz | Ph | 5-i-Pr | H | H | CH₂C(CH₃)₂ | CO₂H | O |
| 31. | 4-Cl-Bz | Me | 5-F | H | H | (CH₂)₂ | CO₂H | O |
| 32. | 4-Cl-Bz | Me | 5-i-Pr | H | H | (CH₂)₂ | CO₂H | O |
| 33. | 4-Cl-Bz | Me | 5-F | H | H | (CH₂)₂ | CO₂H | O |
| 34. | 4-Cl-Bz | t-Bu | 5-i-Pr | H | H | CH₂C(CH₃)₂ | CH₂OH | S |
| 35. | 4-Cl-Bz | t-Bu | 5-i-Pr | H | H | CH₂C(CH₃)₂ | CONH₂ | S |
| 36. | 4-Cl-Bz | t-Bu | 5-i-Pr | H | H | CH₂C(CH₃)₂ | CHO | S |
| 37. | 4-Cl-Bz | t-Bu | 5-i-Pr | H | H | CH₂C(CH₃)₂ | CONH—SO₂Ph | S |
| 38. | 4-Cl-Bz | Ph | 5-i-Pr | H | H | (CH₂)₂ | tetrazol-5-yl | S |
| 39. | 4-Cl-Bz | CH₂CH₂OH | 5-i-Pr | H | H | CH₂C(CH₃)₂ | CO₂H | S |
| 40. | 4-Cl-Bz | CH₂CH₂OH | 5-i-Pr | H | H | CH₂C(CH₃)₂ | CO₂H | SO |

TABLE 1-continued

Novel 3-Hetero-substituted-N-benzyl-indoles

| Ex. | Bnz | R³ | R⁴ | R⁵ | R⁶ | —(CR²R²)ₙ— | E | X |
|---|---|---|---|---|---|---|---|---|
| 41. | 4-Cl-Bz | CH₂CH₂OH | 5-i-Pr | H | H | CH₂C(CH₃)₂ | CO₂H | SO₂ |
| 42. | 4-Cl-Bz | C(CH₃)₂CH₂CO₂H | 5-i-Pr | H | H | CH₂C(CH₃)₂ | CO₂H | S |
| 43. | 4-Cl-Bz | C(CH₃)₂CH₂CO₂Me | 5-i-Pr | H | H | CH₂C(CH₃)₂ | CO₂H | S |
| 44. | 4-Cl-Bz | c-Pr | 5-i-Pr | H | H | CH₂C(CH₃)₂ | CO₂H | S |
| 45. | 4-Cl-Bz | c-Pr | 5-i-Pr | H | H | CH₂C(CH₃)₂ | CO₂H | SO |
| 46. | 4-Cl-Bz | c-Pr | 5-i-Pr | H | H | CH₂C(CH₃)₂ | CO₂H | SO₂ |
| 47. | 4-Cl-Bz | i-Pr | 5-i-Pr | H | H | CH₂C(CH₃)₂ | CO₂H | S |
| 48. | 4-Cl-Bz | i-Pr | 5-i-Pr | H | H | CH₂C(CH₃)₂ | CO₂H | SO |
| 49. | 4-Cl-Bz | i-Pr | 5-i-Pr | H | H | CH₂C(CH₃)₂ | CO₂H | SO₂ |
| 50. | 4-Cl-Bz | C(CH₃)₂CH₂OH | 5-i-Pr | H | H | CH₂C(CH₃)₂ | CO₂H | S |
| 51. | 4-Cl-Bz | 4-Me₂NCH₂-Ph- | 5-i-Pr | H | H | CH₂C(CH₃)₂ | CO₂H | S |
| 52. | 4-Cl-Bz | 4-Me₂NCH₂-Ph- | 5-i-Pr | H | H | CH₂C(CH₃)₂ | CO₂H | SO |
| 53. | 4-Cl-Bz | 4-Me₂NCH₂-Ph- | 5-i-Pr | H | H | CH₂C(CH₃)₂ | CO₂H | SO₂ |
| 54. | 4-Cl-Bz | t-Bu | 5-c-Pr | H | H | CH₂C(CH₃)₂ | CO₂H | S |
| 55. | 4-Cl-Bz | t-Bu | 5-c-Pr | H | H | CH₂C(CH₃)₂ | CO₂H | SO₂ |
| 56. | 4-Cl-Bz | 2-imidazyl | 5-i-Pr | H | H | CH₂C(CH₃)₂ | CO₂H | S |
| 57. | 4-Cl-Bz | 2-imidazyl | 5-i-Pr | H | H | CH₂C(CH₃)₂ | CO₂H | SO |
| 58. | 4-Cl-Bz | 2-imidazyl | 5-i-Pr | H | H | CH₂C(CH₃)₂ | CO₂H | SO₂ |
| 59. | 4-Cl-Bz | 4-imidazyl | 5-i-Pr | H | H | CH₂C(CH₃)₂ | CO₂H | SO |
| 60. | 4-Cl-Bz | 2-(1-Me-imidazyl) | 5-i-Pr | H | H | CH₂C(CH₃)₂ | CO₂H | SO₂ |
| 61. | 4-Cl-Bz | 5-(1-Me-tetrazyl) | 5-i-Pr | H | H | CH₂C(CH₃)₂ | CO₂H | S |
| 62. | 4-Cl-Bz | | 5-i-Pr | H | H | CH₂C(CH₃)₂ | CO₂H | S |
| 63. | 4-Cl-Bz | t-Bu | 5-i-Pr | H | H | CH₂CCH₂CH₂ / CH₂CH₂CH₂ | CO₂H | S |
| 64. | 4-Cl-Bz | 4-pyridyl | 5-i-Pr | H | H | CH₂C(CH₃)₂ | CO₂H | S |
| 65. | 4-Cl-Bz | 2-pyridyl | 5-i-Pr | H | H | CH₂C(CH₃)₂ | CO₂H | S |
| 66. | 4-Cl-Bz | 2-thiazolyl | 5-i-Pr | H | H | CH₂C(CH₃)₂ | CO₂H | S |
| 67. | 4-Cl-Bz | 2-thiazolinyl | 5-i-Pr | H | H | CH₂C(CH₃)₂ | CO₂H | S |
| 68. | 4-Cl-Bz | CH₂-2-pyridyl | 5-i-Pr | H | H | CH₂C(CH₃)₂ | CO₂H | O |
| 69. | 4-Cl-Bz | CH₂-4-pyridyl | 5-i-Pr | H | H | CH₂C(CH₃)₂ | CO₂H | O |
| 70. | 4-Cl-Bz | t-Bu | 5-Ph | H | H | CH₂C(CH₃)₂ | CO₂H | O |
| 71. | 4-Cl-Bz | t-Bu | 5-Ph | H | H | CH₂C(CH₃)₂ | CO₂H | O |
| 72. | 4-Cl-Bz | i-Pr | 5-i-Pr | H | H | CH₂C(CH₃)₂ | CO₂H | O |
| 73. | 4-Cl-Bz | i-Pr | 5-i-Pr | H | H | CH₂C(CH₃)₂ | CO₂H | O |
| 74. | 4-MeOBz | Ph | 5-i-Pr | H | H | CH₂C(CH₃)₂ | CO₂H | S |
| 75. | 4-OHBz | Ph | 5-i-Pr | H | H | CH₂C(CH₃)₂ | CO₂H | SO₂ |

TABLE 1-continued

Novel 3-Hetero-substituted-N-benzyl-indoles

| Ex. | Bnz | R³ | R⁴ | R⁵ | R⁶ | —(CR²R²)ₙ— | E | X |
|---|---|---|---|---|---|---|---|---|
| 76. | 3-I, 4-OHBz | Ph | 5-i-Pr | H | H | CH₂C(CH₃)₂ | CO₂H | SO₂ |
| 77. | 3,4-di-Cl-Bz | t-Bu | 5-i-Pr | H | H | CH₂C(CH₃)₂ | CO₂H | S |
| 78. | 4-Cl-Bz | Ph | 5-Et | H | 7-Me | CH₂C(CH₃)₂ | CO₂H | S |
| 79. | 4-Cl-Bz | Ph | 6-i-Pr | H | H | CH₂C(CH₃)₂ | CO₂H | S |
| 80. | 4-MeO-Bz | n-Bu | 4-Me | H | 6-i-Pr | CH₂C(CH₃)₂ | CO₂H | SO₂ |
| 81. | 4-Cl-Bz | t-Bu | 5-OEt | H | H | CH₂C(CH₃)₂ | CO₂H | S |
| 82. | 2,6-di-Cl-Bz | Ph | 5-i-Pr | H | 7-Me | CH₂C(CH₃)₂ | CO₂H | SO₂ |
| 83. | 4-Cl-Bz | t-Bu | 5-i-Pr | H | 6-Me | CH₂C(CH₃)₂ | CO₂H | S |
| 84. | 3,5-di-Cl-Bz | Ph | 5-i-Pr | H | H | CH₂C(CH₃)₂ | CO₂H | SO₂ |
| 85. | 4-Cl-Bz | 4-MePh | 5-i-Pr | H | H | CH₂C(CH₃)₂ | CO₂H | O |
| 86. | 4,6-di-Cl-Bz | t-Bu | 5-OMe | H | 4-Me | CH₂C(CH₃)₂ | CO₂H | S |
| 87. | 4-Cl-Bz | 4-NH₂-Ph | 5-i-Pr | H | H | CH₂C(CH₃)₂ | CO₂H | SO₂ |
| 88. | 4-Cl-Bz | 4-N₃-Ph | 5-i-Pr | H | H | CH₂C(CH₃)₂ | CO₂H | S |
| 89. | 4-Cl-Bz | 3-NH₂-Ph | 5-i-Pr | H | H | CH₂C(CH₃)₂ | CO₂H | S |
| 90. | 4-Cl-Bz | 3-NHAc-Ph | 5-i-Pr | H | H | CH₂C(CH₃)₂ | CO₂H | SO₂ |
| 91. | 4-Br-Bz | t-Bu | 5-i-Pr | H | H | CH₂C(CH₃)₂ | CO₂H | S |
| 92. | 4-Br-Bz | Ph | 5-i-Pr | H | H | CH₂C(CH₃)₂ | CO₂H | SO |
| 93. | 4-Br-Bz | Ph | 5-MeO | H | 6-Me | CH₂C(CH₃)₂ | CO₂H | SO₂ |
| 94. | 4-I-Bz | Ph | 5-i-Pr | 5-i-Pr | 7-Ac | CH₂C(CH₃)₂ | CO₂H | SO₂ |
| 95. | 4-SMe-Bz | Ph | 4-Me | 5-OEt | 7-OAc | CH₂C(CH₃)₂ | CO₂H | SO₂ |
| 96. | 4-S(O)₂NMe₂ | 4-CN-Ph | 4-N₃ | 5-OEt | 7-OAc | CH₂C(CH₃)₂ | COCH₂OH | S |
| 97. | 4-S(O)₂NMe₂ | 4-Tz-Ph | 4-N₃ | H | H | CH₂C(CH₃)₂ | COCH₂OH | S |
| 98. | 4-Cl-Bz | Ph | 5-C(OH)(CH₃)₂ | H | H | CH₂C(CH₃)₂ | CO₂H | SO₂ |
| 99. | 4-Cl-Bz | t-Bu | 5-CH(CH₃)CH₂OH | H | H | CH₂C(CH₃)₂ | CO₂H | SO₂ |
| 100. | 4-Cl-Bz | t-Bu | 5-C(OH)(CH₃)₂ | H | H | CH₂C(CH₃)₂ | CO₂H | S |
| 101. | 4-Cl-Bz | n-Bu | 5-CH(CH₃)CH₂OH | H | H | CH₂C(CH₃)₂ | CO₂H | S |
| 102. | 4-Cl-Bz | n-Bu | 5-i-Pr | H | H | CH₂C(CH₃)₂ | CO₂H | S |
| 103. | 4-Cl-Bz | n-Bu | 5-i-Pr | H | H | CH₂C(CH₃)₂ | CO₂H | SO₂ |
| 104. | 4-Cl-Bz | Cyclohexyl | 5-i-Pr | H | H | CH₂C(CH₃)₂ | CO₂H | S |
| 105. | 4-Cl-Bz | Cyclohexyl | 5-i-Pr | H | H | CH₂C(CH₃)₂ | CO₂H | SO |
| 106. | 4-Cl-Bz | Cyclohexyl | 5-i-Pr | H | H | CH₂C(CH₃)₂ | CO₂H | SO₂ |
| 107. | 4-Cl-Bz | Ph | 5-i-Pr | H | H | CH₂C(CH₃)₂ | CONHCH₂CO₂H | S |
| 108. | 4-Cl-Bz | CH₂-c-Pr | 5-i-Pr | H | H | CH₂C(CH₃)₂ | CO₂H | SO₂ |
| 109. | 4-Cl-Bz | CH₂-c-Pr | 5-i-Pr | H | H | CH₂C(CH₃)₂ | CONHCH₂CO₂H | S |
| 110. | 4-Cl-Bz | Ph | 5-i-Pr | H | H | CH₂C(CH₃)₂ | CONHCH₂CO₂H | SO₂ |
| 111. | 4-Cl-Bz | t-Bu | 5-i-Pr | H | H | CH₂C(CH₃)₂ | CONHCH₂CO₂H | S |
| 112. | 4-Cl-Bz | n-Bu | 5-i-Pr | H | H | CH₂C(CH₃)₂ | CON(Me)₂ | SO₂ |
| 113. | 4-Cl-Bz | t-Bu | 5-i-Pr | H | H | CH₂C(CH₃)₂ | CONH₂ | s |
| 114. | 4-OH-Bz | CH₂-c-Pr | 5-i-Pr | H | H | CH₂C(CH₃)₂ | CO₂H | s |
| 114a | 4-OH-Bz | t-Bu | 5-i-Pr | H | H | CH₂C(CH₃)₂ | CO₂H | s |
| 115a | 4-NO₂-Bz | Ph | 5-i-Pr | H | H | CH₂C(CH₃)₂ | CO₂CH₃ | SO₂ |

TABLE 1-continued

Novel 3-Hetero-substituted-N-benzyl-indoles

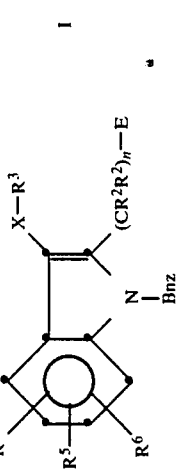

| Ex. | Bnz | $R^3$ | $R^4$ | $R^5$ | $R^6$ | $-(CR^2R^2)_n-$ | E | X |
|---|---|---|---|---|---|---|---|---|
| 115b | 4-NH$_2$-Bz | Ph | 5-i-Pr | H | H | CH$_2$C(CH$_3$)$_2$ | CO$_2$H | SO$_2$ |
| 116 | 4-Cl-Bz | 5-Cl-Benzo-thiazol-2-yl | 5-i-Pr | H | H | CH$_2$C(CH$_3$)$_2$ | CO$_2$H | S |
| 117 | 4-Cl-Bz | t-Bu | 5-i-Pr | H | H | CH(CH$_3$) | CO$_2$H | S |
| 118 | 4-CH$_3$SO$_2$-Bz | t-Bu | 5-i-Pr | 7-Cl | H | CH$_2$C(CH$_3$)$_2$ | CO$_2$H | S |
| 119 | 4-Cl-Bz | CH$_2$-c-Pr | 5-i-Pr | 4-CF$_3$ | H | CH$_2$C(CH$_3$)$_2$ | CO$_2$H | O |
| 120 | 4-Cl-Bz | t-Bu | 5-i-Pr | H | 7-Br | CH$_2$C(CH$_3$)$_2$ | CO$_2$H | O |
| 121 | 4-Cl-Bz | 2-Quinolinyl | 5-i-Pr | H | H | CH$_2$C(CH$_3$)$_2$ | CO$_2$H | S |
| 122 | 4-Cl-Bz | t-Bu | 5-i-Pr | 4-SEt | H | CH$_2$C(CH$_3$)$_2$ | CH$_2$OCOCH$_2$CO$_2$H | S |
| 123 | 4-Cl-Bz | t-Bu | 5-i-Pr | 7-COMe | H | CH$_2$C(CH$_3$)$_2$ | CH$_2$NHCOCH$_2$CO$_2$H | S |
| 124 | 4-Cl-Bz | t-Bu | 5-i-Pr | H | H | CH$_2$C—(CH$_2$)$_3$—CH$_2$ | CO$_2$H | S |
| 125 | 4-MeO-Bz | 4-N$_3$-Ph | 5-i-Pr | H | H | CH$_2$C(CH$_3$)$_2$ | CO$_2$H | SO$_2$ |
| 126 | 3-CN-Bz | t-Bu | 5-i-Pr | 4-S(O)$_2$-Me | H | CH$_2$C(CH$_3$)$_2$ | CO$_2$H | S |
| 127 | 4-Cl-Bz | CH$_2$CH$_2$CH=CH$_2$ | 5-i-Pr | H | H | CH$_2$C(CH$_3$)$_2$ | CO$_2$H | S |
| 128 | 4-Cl-Bz | Bz | 5-i-Pr | H | H | CH$_2$C(CH$_3$)$_2$ | CO$_2$H | S |
| 129 | 4-Cl-Bz | 2-(i-Pr)Ph | 5-i-Pr | H | H | CH$_2$C(CH$_3$)$_2$ | CO$_2$H | S |
| 130 | 4-Cl-Bz | 2-(i-Pr)Ph | 5-i-Pr | H | H | CH$_2$C(CH$_3$)$_2$ | CO$_2$H | SO$_2$ |
| 131 | 4-Cl-Bz | t-Bu | 5-i-Pr | H | H | CH$_2$C(CH$_3$)$_2$ | CO$_2$H | S |

The invention is further defined by reference to the following examples, which are intended to be illustrative and not limiting.

All temperatures are in degrees Celsius.

PREPARATION OF STARTING MATERIALS

Preparation 1

1-(p-chlorobenzyl)-1-[4-(i-propyl)phenyl]hydrazine hydrochloride

Method A

A mixture of 17.9 g of 4-iso propylphenyl hydrazine, 300 mL of dry toluene, 19.1 q 4-chlorobenzyl chloride and 1.16 g tetra-n-butylammonium bromide was heated at reflux for 4 h. The reaction mixture was then cooled to room temperature, diluted with ether and 0.1 N NaOH (100 mL) added. The organic layer was separated, washed with water and brine and dried over MgSO$_4$. Filtration and concentration in vacuo gave an orange oil. This material was dissolved in a 2:1 mixture of hexaneether and treated with dry HCl gas. Collection of the resultant solid by vacuum filtration gave the title compound, which was used as such in subsequent reactions.

Method B

A dry 5 l flask, equipped with mechanical stirring and a nitrogen inlet, was charged with 4-isopropylphenylhydrazine hydrochloride (186.6 gm, 1 mol) and toluene (1.2 1), then flushed with nitrogen. Triethylamine (202 gm, 2 mol), tetra-n-butylammonium bromide (10 gm, 0.03 mol) and 4-chlorobenzyl chloride (160 gm, 1 mol) were then added and the mixture heated at reflux for 4 h. The reaction was allowed to cool to room temperature, filtered, then concentrated to about 600 ml to remove residual triethylamine.

Toluene (2.5 1) and ether (1.2 1) were added, the mixture cooled to 0° C., then treated with a solution of HCl (1 mol) in toluene. The resultant hydrochloride salt was allowed to crystalize overnight at 0° C. and suction filtered. Washing with ether and drying (25° C./0.4 torr) yielded the title product.

Preparation 2

1-(p-chlorobenzyl)-1-[4-(t butyl)phenyl]hydrazine hydrochloride

Step 1: A mixture of 51 q tert butylaniline, 700 mL toluene and 53 q 4 chlorobenzaldehyde was heated at reflux with removal of water. After 1 h the solvent was removed in vacuo and replaced with 800 mL of dry tetrahydrofuran. A solution containing 21.5 q of sodium cyanoborohydride in 100 mL of methanol was then added and the resultant mixture acidified by the slow addition of acetic acid (20 mL).

After stirring overnight the reaction mixture was cooled to 0° and excess 3 N hydrochloric acid added. The resultant precipitate was collected by vacuum filtration, washed twice with ether and dried in vacuo to yield N-(p-chlorobenzyl)4-t-butylaniline hydrochloride salt.

Step 2: A suspension of 50 q of the hydrochloride salt from Step 1, 500 mL water, 250 mL ether and 170 mL of 1 N hydrochloric acid was treated with a solution of 12.3 q sodium nitrite in 50 mL of water. After stirring for 2 h at room temperature the reaction mixture was extracted twice with ether. The combined extracts were washed with water and dried over MgSO$_4$. Filtration and concentration gave N-nitroso-N-(p-chlorobenzyl)-4-t-butylaniline.

Step 3: A cold (0°), stirred mixture of 25 q of the nitroso derivative from Step 3 and 500 mL tetrahydrofuran, under nitrogen, was treated with 285 mL of a 1 M solution of diisobutylaluminum hydride in toluene. Stirring was continued at room temperature for two days then at reflux for 4 h. The reaction mixture was cooled and carefully poured into dilute hydrochloric acid. The resultant mixture was extracted with ethyl acetate (3×) and the combined extracts were evaporated to dryness. The material thus obtained was dissolved in a mixture of hexane and ethyl acetate (1:1) and treated with dry HCl gas. Collection of the resultant solid by vacuum filtration gave the title compound, which was used without further purification.

Additional hydrazine starting materials are known; e.g., see Example 1 of EP 166,591.

Preparation 3

1-(p-chlorobenzyl)-1-(4-biphenyl)hydrazine hydrochloride

Following the procedure of Preparation 2, but using 4 aminobiphenyl as the starting material, the title compound was obtained.

Preparation 4

α-Hetero-Ketone Starting Materials

A. Methyl 2,2-Dimethyl-4-oxo-5-phenylthiopentanoate (Compound 1)

Step 1: A stirred solution containing 10 q of 2,2--dimethyl-4-oxo-pentanoic acid in 200 mL of dry methanol was treated with 3.75 mL of bromine dropwise over a 15 min period. The mixture was then stirred at room temperature for 2 h and at reflux for 2 h. After cooling to room temperature, water and solid sodium bicarbonate were added and the mixture diluted with ethyl acetate. The organic layer was separated and washed with brine and dried over MgSO$_4$. Filtration and concentration gave an orange oil which was redried in ether over MgSO$_4$. Isolation and distillation (87°-95°, 1.3 torr) gave methyl 5 bromo-2,2-dimethyl-4-oxopentanoate. IR (film) 2958, 1772 and 1720 cm$^{-1}$; $^1$H NMR (250 MHz, CDCl$_3$) δ 1.26 (s, 6H), 2.93 (s, 2H), 3.67 (s, 3H), 3.86 (s, 2H).

Step 2: To a cold (0°), stirred suspension of sodium hydride (365 mg) in 66 mL dry tetrahydrofuran, under nitrogen, was added 1.4 g thiophenol. Stirring was continued at 0° for 30 min. and at room temperature for 30 min. The resultant white suspension of sodium thiophenoxide was cooled to −78° and a solution containing 3.0 q of methyl 5-bromo-2,2-dimethyl-4-oxopentanoate from Step 2 in 10 mL dry tetrahydrofuran was then added. The reaction mixture was stirred at −78° for 15 min. and at ambient temperature for 6 h then quenched with saturated aqueous ammonium sulfate. Ether was added, the organic layer separated and washed with water (2×) and brine and dried over MgSO$_4$. Filtration and concentration gave a yellow oil which was purified by flash chromatography on silica gel. Elution of the column with a 4 to 1 mixture of hexane and ethyl acetate gave the title product. IR (film) 3040, 2960, 1721 and 1145 cm$^{-1}$; $^1$H NMR (250 MHz, CDCl$_3$) δ 1.18 (s, 6H), 2.91 (s, 2H), 3.60 (s, 3H), 3.63 (s, 2H), 7.13-7.35 (m, 5H).

B. Other α-Hetero-Ketones

Using procedures analogous to those above, the hetero-ketones 2-10, 12, and 14-21 of Table 4-1 were prepared.

C. Methyl-5-methoxy-4-oxopentanoate (Compound 13)

To a solution of 6.75 q (0.05 mole) of methyl (3-chloroformyl)propionate in 150 ml diethyl ether, was added 0.075 mole diazomethane in ether at 0° C. The reaction was stirred at room temperature for 3 hours, after which it was treated with 2 ml glacial acetic acid. 40 ml of a 1:1 solution of anhydrous methanol and ether were added dropwise. The solvents were removed after 24 hours by vacuum distillation and the product was isolated by passage through a small silica gel column, followed by short-path vacuum distillation (1 mm Hq, 60°-80° C.).

Compound 11 of Table 4-1 was prepared by an analogous procedure.

D. Methyl-5-t-Butylthio-2,2-dimethyl-4-oxopentanoate (Compound 6)

Step 1: A 5 L 3-necked flask equipped with an air driven stirrer, pressure equalizing addition funnel, and nitrogen inlet was charged with diisopropylamine (136 gm, 1.34 mol) and dry tetrahydrofuran (1.5 1). The mixture was cooled to 0° C. and a 1.6M solution of butyl lithium in hexane (800 ml, 1.28 mol) was then added over a 30 min period and stirring was continued for an additional 15 min.

The resultant solution of lithium diisopropylamide (1.28 mol) was then treated with a solution of ethyl isobutyrate (134 gm, 1.16 mol) in 300 ml of dry tetrahydrofuran over a period of 1 h. The reaction mixture was then allowed to warm to room temperature and stirred for 18 h. 2,3-Dichloro-1-propene (142 gm, 1.28 mol) was then added at 0° C. and the resultant solution stirred at room temperature for 6 h.

The reaction mixture was then cooled to 0° C., quenched with saturated aqueous ammonium chloride, and diluted with ethyl acetate (approx. 2 L). The organic layer was separated, washed with 1N HCl (1 L), water (2×500 ml), brine (1 L) and dried over MgSO4. Filtration and concentration gave a brown oil which was purified by distillation (bp 69°-78° C., 20 Torr) to give 200 gm (90%) of pure (250 MHz NMR) ethyl 4-chloro-2,2-dimethyl-4- pentenoate.

Step 2: A 3 L 3-necked flask, equipped with a magnetic stirrer and thermometer, was charged with 4-chloro-2,2-dimethyl-4-pentenoate from step 1 (1.5 mole), methanol (1.13 L), and water (0.37 L) and cooled to 0° C. Bromine (1.55 mole) was then added dropwise over a 1 h period. The resultant yellow solution was then stirred at room temperature for 90 min. Ethyl acetate (4 L) and water were added. The organic layer was separated, washed with water, 1N NaOH (3×), water and brine and dried over MgSO4. Filtration and concentration gave a yellow liquid which was purified by distillation (bp 83°-112°, 1.2 Torr) to afford 284 gm of a colorless oil. This material was shown by $^1$H NMR to contain a mixture of methyl 5-bromo-2,2-dimethyl-4-oxopentanoate ( 90%) and 5-chloro-2,2-dimethyl-4-oxopentanoate ( 10%) and was used in the next step without further purification.

Step 3: To a cold (0° C.) stirred solution of the bromoketone from step 2 (1.17 mole), in 800 mL of dry tetrahydrofuran, were sequentially added 2-methyl-2-propylthiol (1.23 mole) and triethylamine (1.41 mole). The reaction mixture was then allowed to warm to room temperature. After 18 h, ethyl acetate (2.5 L) was added and the mixture washed with water, 1N HCl (2×), water and brine and dried over MgSO4. Filtration and concentration afforded a pale yellow oil which, after distillation (110°-132° C., 1.0 Torr), gave the title product.

TABLE 4-1

α-Hetero-Ketones

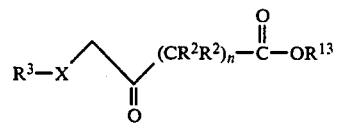

| Compound No. | $R^3$ | $-(CR^2R^2)_n-$ | X | $R^{13}$ | Compound Name |
|---|---|---|---|---|---|
| 2 | Me | $-(CH_2)-$ | S | Et | Ethyl 4-methylthio-3-oxo-butanoate |
| 3 | Ph | $-(CH_2)-$ | S | Et | Ethyl 3-oxo-4-phenylthiobutanoate |
| 4 | Me | $-CH_2C(CH_3)_2-$ | S | Me | Methyl 2,2-dimethyl-5-methylthio-4-oxopentanoate |
| 5 | Ph | $-CH_2C(CH_3)_2-$ | S | Me | Methyl 2,2-dimethyl-4-oxo-5-phenylthiopentanoate |
| 6 | t-Bu | $-CH_2C(CH_3)_2-$ | S | Me | Methyl 5-t-butylthio-2,2-dimethyl-4-oxopentanoate |
| 7 | Me | $-(CH_2)_2-$ | S | Me | Methyl 5-methylthio-4-oxo-pentanoate |
| 8 | Ph | $-(CH_2)_2-$ | S | Me | Methyl 4-oxo-5-ohenylthiopentanoate |
| 9 | Ph | $-(CH_2)_2C(CH_3)_2-$ | S | Me | Methyl 2,2-dimethyl-5-oxo-6-phenylthiohexanoate |
| 10 | Ph | $-CH_2C(CH_3)_2-$ | O | Me | Methyl 2,2-dimethyl-4-oxo-5-phenoxypentanoate |
| 11 | Me | $-CH_2C(CH_3)_2-$ | O | Me | Methyl 2,2-dimethyl-5-methoxy-4-oxopentanoate |
| 12 | Ph | $-(CH_2)_2-$ | O | Me | Methyl 4-oxo-5-phenoxypentanoate |
| 13 | Me | $-(CH_2)_2-$ | O | Me | Methyl 5-methoxy-4-oxopentanoate |
| 14 | $CH_2$-c-Pr | $-CH_2C(CH_3)_2-$ | S | Me | Methyl 2,2-dimethyl-4-oxo-5-(1-cyclopropylmethylthio)pentanoate |
| 15 | $CH_2$-c-$C_6H_{11}$ | $-CH_2C(CH_3)_2-$ | S | Me | Methyl 2,2-dimethyl-4-oxo-5-(1-cyclohexylmethylthio)pentanoate |
| 16 | 5-Cl-benzo-thiazol-2-yl | $-CH_2C(CH_3)_2-$ | S | Me | Methyl 2,2-dimethyl-4-oxo-5-(5-chlorobenzothiazol-2-ylthio)pentanoate |
| 17 | $-CH_2CH_2CH=CH_2$ | $-CH_2C(CH_3)_2-$ | S | Me | Methyl 2,2-dimethyl-4-oxo-5-(1-buten-4-ylthio)pentanoate |

TABLE 4-1-continued

α-Hetero-Ketones $$R^3-X\underset{O}{\overset{}{\diagdown\!\!\!\diagup}}(CR^2R^2)_n-\overset{O}{\underset{}{\overset{\|}{C}}}-OR^{13}$$

| Compound No. | $R^3$ | $-(CR^2R^2)_n-$ | X | $R^{13}$ | Compound Name |
|---|---|---|---|---|---|
| 18 | t-Bu | $-CH_2C(CH_2)_3-CH_2$ (cyclic) | S | Me | Methyl 1-[3-(t-butylthio)-2-oxo-prop-1-yl]cyclopentane carboxylate |
| 19 | Bz | $-CH_2C(CH_3)_2-$ | S | Me | Methyl 2,2-dimethyl-4-oxo-5-(benzyl-thio)pentanoate |
| 20 | n-Bu | $-CH_2C(CH_3)_2-$ | S | Me | Methyl 2,2-dimethyl-4-oxo-5-(butyl-thio)pentanoate |
| 21 | 2-(i-$C_3H_7$)$C_6H_4$ | $-CH_2C(CH_3)_2-$ | S | Me | Methyl 2,2-dimethyl-4-oxo-5-(2-i-propylphenylthio)pentanoate |

Preparation 5

Ethyl 5-chloro-3-phenylthioindole-2-carboxylate

To a cold (0°), stirred solution of ethyl 5-chloroindole-2-carboxylate (223 mg) in 4.5 mL dry tetrahydrofuran, under argon, was added 0.55 mL of a solution of ethylmagnesium bromide in ether. The resultant mixture was stirred for 30 min then cooled to $-78°$. Solid S-phenyl benzenethiosulfonate (300 mg) was added and the mixture stirred at $-78°$ for 30 min and 0° for 1 h. The mixture was then diluted with ether and saturated aqueous ammonium chloride added. The organic layer was separated, washed with water and brine and dried over $MgSO_4$. Filtration and concentration gave a yellow oil which was purified by flash chromatography on silica gel. Elution with hexane ethyl acetate (85:15) gave the title product. IR (KBr) 3340, 3060, 2994, 1680, 1508, 1263 and 738 cm$^{-1}$; $^1H$ NMR (250 MHz, $CDCl_3$) δ 1.28 (t, 3H, J = 7 Hz), 4.39 (q, 2H, J = 7 Hz), 7.08–7.24 (m, 5H), 7.27 (dd, 1H, J = 9 and 2 Hz), 7.39 (d, 1H, J = 9 Hz), 7.60 (d, 1H, J = 2 Hz).

Preparation 6

5-Chloro-3-phenylthioindole-2-carboxylic acid

To 57 mg of ethyl 5-chloro-3-phenylthioindole-2-carboxylate from Preparation 5 in 1.7 mL of dry tetrahydrofuran, under argon, was added 48 mg of solid potassium trimethylsilanolate. The resultant mixture was stirred at room temperature for 20 h. Ethyl acetate and 1 N HCl were then added. The organic layer was washed with brine (2×) and dried over $MgSO_4$. Filtration and concentration gave a yellow gum which was triturated with ether-hexane to give the title compound. $^1H$ NMR (250 MHz, $CDCl_3$) δ 7.09–7.18 (m, 3H), 7.20–7.25 (m, 2H), 7.30 (dd, 1H, J = 8.6 and 2.0 Hz), 7.43 (d, 1H, J = 2.0 Hz), 7.52 (d, 1H, J = 8.6 Hz).

Preparation 7

4-Methylthiophenyl hydrazine hydrochloride

4-Methylthioaniline (13.9 q) was added dropwise to cold HCl (6N, 50 mL) and stirred for 5 min in an ice bath. A solution of $NaNO_2$ in water (7.25 q, 15 mL) was then added dropwise and stirred for 15 min. The cold diazonium salt was then cannulated into a stirred cold solution of $Na_2S_2O_4$ in water (50 q, 250 mL). After 20 min, ether (200 mL) was added and the reaction mixture basified with NaOH (10N). The ether layer was decanted, washed with brine, dried over $Na_2SO_4$ and HCl gas was passed through the ether solution to form the hydrochloride salt which precipitated out. After filtration, there was obtained pure title product.

The following phenyl hydrazines were similarly prepared:

2-isopropylphenylhydrazine hydrochloride
2-methylthiophenylhydrazine hydrochloride
2,4-dimethylphenylhydrazine hydrochloride
4-methoxy-2-methylphenylhydrazine hydrochloride Other phenylhydrazines can also be prepared by the method described by Demers and Klaubert, Tetrahedron Letters, 28, 4933 (1987).

PREPARATION OF FINAL PRODUCTS

EXAMPLE 1

Ethyl 1-(p-chlorobenzyl)-5-chloro-3-thiophenylindole-2-carboxylate

To a cold ($-78°$), stirred solution containing 664 mg of ethyl 5-chloro-3-thiophenylindole-2-carboxylate from Preparation 5 in 3.5 mL of dry tetrahydrofuran, under argon, was added 3.5 mL of a 0.62 M solution of potassium hexamethylsilamide in toluene. The reaction mixture was stirred at $-78°$ for 1 h and at 0° for 1 h then recooled to $-78°$. 0.75 mL of g chlorobenzyl chloride, 1.0 mL of hexamethylphosphoric triamide and 20 mg of tetra-n-butylammonium bromide were then added. The resultant mixture was allowed to warm to room temperature and stirred for 18 h. Saturated aqueous ammonium chloride and ether were added. The ether layer was separated, washed with water, 10% aqueous cupric sulfate, water and brine and dried over $MgSO_4$.

Filtration and concentration gave a solid which was purified by flash chromatography on silica gel. Elution of the column with a mixture of hexane-ethylacetate (9:1) gave the title product, mp 95.5°–96°.

Analysis calculated for $C_{24}H_{19}Cl_2CO_2S$: C, 63.16; H, 4.20; N, 3.07. Found: C, 63.35; H, 4.44; N, 3.01.

EXAMPLE 2

1-(p Chlorobenzyl)-5-chloro-3-thiophenylindole-2-carboxylic acid

Following the procedure of Preparation 6, but using ethyl 1-(p-chlorobenzyl)-5-chloro-3-thiophenylindole- 2-carboxylate from Example 1 as the starting material and tetrahydrofuran as the solvent, the title compound was prepared, mp 185°–188° (dec.).

EXAMPLE 3

Ethyl 1-(p Chlorobenzyl)-5-fluoro-3-methylthioindole-2-acetate

To 2.40 g of ethyl 4-methylthio-3--oxobutanoate in 35 mL tert butanol was added 4.30 g of 1-p-chlorobenzyl)-1-(4-fluorophenyl) hydrazine hydrochloride. The reaction mixture was refluxed under nitrogen for 16 h. The reaction mixture was then evaporated to dryness and the residue suspended in ether. The ether layer was washed with 1 N HCl (2×), water and brine and dried over $MgSO_4$. Filtration and concentration gave a pale yellow oil which was purified by flash chromatography on silica gel. Elution of the column with a mixture of hexane-ethyl acetate (85:15) gave the title compound as a solid, mp 118°–119°.

EXAMPLE 4

1-(p-Chlorobenzyl)-5-fluoro3-methylthioindole-2-acetic acid

Following the procedure of Preparation 6, but using ethyl 1-(p-chlorobenzyl)-5-fluoro-3-methylthioindole-2-acetate from Example 3 as the starting material and tetrahydrofuran as the solvent, the title compound was prepared, mp 154 155° C. (dec.).

EXAMPLE 5

1-(p Chlorobenzyl)-5-fluoro-3-methylsulfonylindole-2-acetic acid

To 200 mg of 1-(p-chlorobenzyl)-5-fluoro-3-methylthioindole-2-acetic acid from Example 4 in a mixture of 3 mL water and 3 mL ethanol was added 1.6 q of oxone. After stirring for 6 h the reaction mixture was diluted with brine and ether. The ether layer was washed with 1 N HCl, and brine and dried over $MgSO_4$. Filtration and concentration gave the title compound, mp 202°–202.5°.

EXAMPLE 6

1-(p Chlorobenzyl)-5-fluoro methyl-3-methylthioindole-2-acetic acid

Step 1: To a cold (−78°), stirred solution of 560 mg of ethyl 1-(p-chlorobenzyl)-5-fluoro-3-methylthioindole-2-acetate from Example 3 in 6 75 mL dry tetrahydrofuran, under argon, was added 2.72 mL of a 0.63 M solution of potassium hexamethyldisilazide in toluene. After 2 h at −78°, 123 μL of methyl iodide was added and the mixture stirred at −78° for 30 min and 0° for 1 h. 10% aqueous sodium bisulfate and ether were then added. The organic layer was separated, washed with 10% aqueous sodium bisulfate, water and brine and dried over $MgSO_4$. Filtration and concentration gave a pale yellow oil which was purified by flash chromatography on silica gel. Elution with a mixture of hexane ethyl acetate (85:15) gave an indole derivative, mp 131°–132°.

Step 2: Following the procedure of Preparation 6, but using ethyl 1-(p-chlorobenzyl)-5-fluoro-α-methyl-3-methylthioindole-2-acetate from Step 1 as starting material and tetrahydrofuran as solvent, the title compound was prepared, mp 136°–140°.

Analysis calculated for $C_{19}H_{17}ClFNO_2S$: C, 60.39; H, 4.53; N, 3.71; Found: C, 60.13; H, 4.57; N, 3.65.

EXAMPLE 7

1-(p Chlorobenzyl)-α,α-dimethyl-5-fluoro-3-methylthioindole-2-acetic acid

Following the procedure of Example 6, but using ethyl 1-(p-chlorobenzyl)-5-fluoro methyl-3-methylthioindole-2-acetate, from Example 6, Step 1, as the starting material and tetrahydrofuran as solvent the title compound was prepared. IR (KBr) 3430, 1708, 1482 and 1167 cm$^{-1}$; $^1$H NMR (250 MHz, $CDCl_3$) δ 1.81 (s, 6H), 2.29 (s, 3H), 5.35 (s, 2H), 6.82 (d, 2H, J =8.4 Hz), 6.85 (m, 2H), 7.22 (d, 2H, J =8.4 Hz), 7.46 (d, 1H, J =9.5 Hz).

EXAMPLE 8

1-(p-Chlorobenzyl)-5-fluoro-3-phenylthioindole-2-acetic acid

Following the procedures of Examples 3 and 4, but using 1-(p-chlorobenzyl)-1-(4-fluorophenyl)hydrazine hydrochloride and ethyl 3-oxo-4-phenylthiobutanoate as the starting material, the title compound was prepared, mp 167.5°–168.5°.

Analysis calculated for $C_{23}H_{17}ClFNO_2S$: C, 64.86; H, 4.02; N, 3.29; Found: C, 64.72; H, 4.21; N, 3.15.

EXAMPLE 9

1-(p-Chlorobenzyl)-5-fluoro-α-methyl-3-phenylthioindole-2-acetic acid

Following the procedure of Example 6, but using ethyl 1-(p-chlorobenzyl)-5-fluoro-3-phenylthioindole-2-acetate (Example 8, Step 1) as the starting material and tetrahydrofuran as the solvent, the title compound was prepared, mp 80°–82°.

EXAMPLE 10

1-(p-Chlorobenzyl)-3-phenylthio-5-(i-propyl)-indole-2-acetic acid

Step 1: To 229 mg of ethyl 3-oxo-4-phenylthiobutanoate in 3 mL of t-butanol was added 300 mg of 1-(p-chlorobenzyl)-1-(4-i-propylphenyl)hydrazine hydrychloride. The reaction was refluxed under nitrogen for 2 h. The reaction mixture was then evaporated to dryness and the residue suspended in ether, washed with water, 1 N HCl (2×), water and brine and dried over $MgSO_4$. Filtration and concentration gave a yellow oil which was purified by flash chromatography on silica gel. Elution with a mixture of hexane ethyl acetate (85:15) gave ethyl 1-(p-chlorobenzyl)-3-phenylthio-5-(i-propyl)-indole-2-acetate as a solid.

Analysis calculated for $C_{28}H_{28}O_2ClNS$: C, 70.35; H, 5.90. Found: C, 70.69; H, 6.20.

Step 2: To 100 mg of the ethyl ester from Step 1 in 1.0 mL tetrahydrofuran and 0.5 mL methanol was added 0.5 mL of 2.0 N LiOH at room temperature. After 45 min 1 N HCl and ethyl acetate were added. The organic layer was separated, washed with brine and dried over $MgSO_4$. Filtration and concentration gave the title compound as a white solid which was triturated with hexane and filtered, mp 151°–153°.

Analysis calculated for $C_{26}H_{24}ClNO_2S$: C, 69.39; H, 5.38; N, 3.11; Found: C, 69.18; H, 5.42; N, 3.04

EXAMPLE 11

1-(p Chlorobenzyl)-α-methyl-3-phenylthio-5-(i-propyl)indole-2-acetic acid

Step 1: Following the procedure of Example 6, Step 1, but using ethyl 1-(p-chlorobenzyl)-3-phenylthio-5-(i-propyl)-indole-2-acetate (Example 10, Step 1) as the starting material, lithium diisopropylamide as base, and tetrahydrofuran as solvent, ethyl 1-(p-chlorobenzyl)-α-methyl-3-phenylthio 5 (i propyl)-indole-2-acetate was prepared.

Analysis calculated for $C_{29}H_{30}ClNO_2S$: C, 70.78; H, 6.14; Found: C, 70.86; H, 6.21.

Step 2: To 306 mg of the ethyl ester from Step 1 in 3 mL tetrahydrofuran and 1.5 mL methanol was added 1.5 mL of 2 N LiOH. After 1 h at reflux the mixture was cooled to room temperature, acidified with 1 N HCl and diluted with ether. The ether layer was washed with brine (2×) and dried over $MgSO_4$. Filtration and concentration gave the title compound, mp 181°–181.5°.

EXAMPLE 12

1-(p-Chlorobenzyl)-5-(t-butyl)-3-phenylthio-indole-2-acetic acid

Following the procedure of Example 10, but using 1-(p-chlorobenzyl)-1-(4-t-butylphenyl)hydrazine hydrochloride and ethyl 3-oxo-4-phenylthiobutanoate as starting materials and t-butanol as the solvent, the title compound was prepared, mp 148°–150° C.

EXAMPLE 13

1-(p-Chlorobenzyl)-5-(t butyl)-3-phenylsulfinylindole-2-acetic acid

To a cold (−10°) solution of 1-(p-chlorobenzyl)-5-(t-butyl)-3-phenylthioindole-2-acetic acid (67 mg) from Example 12 in 1.45 mL dry methylene chloride, under nitrogen, was added 34 mg of m-chloroperbenzoic acid. The reaction mixture was stirred at −10° for 1 h and room temperature for 30 min. The reaction mixture was then diluted with ether and washed with water (2×) and brine and dried over $MgSO_4$. Filtration and concentration gave a solid which was passed through a short column of silica gel. Elution with ethyl acetate gave the title compound, mp 160°–161° (dec.).

EXAMPLE 14

1-(p-Chlorobenzyl)-5-(t-butyl)-3-phenylsulfonylindole-2-acetic acid

Following the procedure of Example 5, but using 1-(p-chlorobenzyl)-5-(t-butyl)-3-phenylthio-2-indole-2-acetic acid from Example 12 as the starting material and a mixture of ethanol and water as solvent, the title compound was prepared, mp 177°–179° (dec.).

EXAMPLE 15

1-(p-Chlorobenzyl)-5-fluoro-3-phenylthioindole-2-propanoic acid

Following the procedure of Example 10, but using 1-(p-chlorobenzyl)-1-(4-fluorophenyl)hydrazine hydrochloride and methyl-4-oxo-5-phenylthiopentanoate as starting materials and t butanol as the solvent, the title compound was prepared, mp 138°–139°.

EXAMPLE 16

1-(p-Chlorobenzyl)-3-phenylthio-5-(i-propyl)-indole-2-propanoic acid

Following the procedure of Example 10, but using 1-(p-chlorobenzyl)-1-(4-i-propylphenyl) hydrazine hydrochloride and methyl-4-oxo-5-phenylthiopentanoate as starting materials and t butanol as the solvent, the title compound was prepared, mp 149°–150°.

Analysis calculated for $C_{27}H_{26}ClNO_2S$: C, 69.89; H, 5.64; N, 3.02; Found: C, 69.60; H, 5.73; N, 2.93.

EXAMPLE 17

1-(p Chlorobenzyl)-5-fluoro-3-methylthioindole-2-propanoic acid

Following the procedure of Example 10, but using 1-(p-chlorobenzyl)-1-(4-fluorophenyl)hydrazine hydrochloride and methyl-5-methylthio-4-oxopentanoate as starting materials and t-butanol as the solvent, the title compound was prepared. $^1H$ NMR (250 MHz, $CDCl_3$) δ 2.29 (s, 3H), 2.58 (broad t, 2H, J=7.8 Hz), 3.23 (broad t, 2H, J=7.8 Hz), 5.37 (s, 2H), 6.87 (d, 2H, J=8.5 Hz), 6.89–6.95 (m, 1H), 7.08 (dd, 1H, J=4.3 and 8.9 Hz), 7.25 (d, 2H, J=8.5 Hz), 7.40 (d,d, 1H, J=2.6 and 9.4 Hz).

EXAMPLE 18

1-(p-Chlorobenzyl)-α,α-dimethyl-5-fluoro-3-phenylthioindole-2-propanoic acid Following the procedure of Example 10, but using 1-(p-chlorobenzyl)-1-(4-fluorophenyl)hydrazine hydrochloride and methyl 2,2-dimethyl-4-oxo-5-phenylthiopentanoate as starting materials and hydrolysis at reflux, the title compound was prepared, mp 162°–163°.

Analysis calculated for $C_{26}H_{23}ClFNO_2S$: C, 66.72; H, 4.95; N, 3.00; Found: C, 66.83; H, 5.02; N, 2.94.

EXAMPLE 19

1-(p-Chlorobenzyl)-α,α-dimethyl-3-phenylthio-5-(i-propyl)-indole-2-propanoic acid Following the procedure of Example 10, but using 1-(p-chlorobenzyl)-1-[4-(i-propyl)phenyl]hydrazine hydrochloride and methyl-2,2-dimethyl-4-oxo-5-phenylthiopentanoate as starting material and hydrolysis at reflux, the title compound was prepared, mp 162°–165°.

EXAMPLE 20

1-(p Chlorobenzyl)-α,α-dimethyl-3-phenylsulfinyl-5-(i-propyl)-indole-2-propanoic acid Step 1: To a cold (−10°), stirred solution containing 255 mg of methyl 1-(p-chlorobenzyl)-α,α-dimethyl-3-phenylthio-5-(i-propyl)-indole-2-propanoate from Example 19, Step 1, in 5 mL dry methylene chloride, under nitrogen, was added 118 mg of m-chloroperbenzoic acid. The reaction mixture was warmed to 0° over a period of 1 h then quenched with 1 N NaOH and diluted with ether. The organic layer was washed with 1 N NaOH (2×), brine (2×) and dried over $MgSO_4$. Filtration and concentration gave a pale yellow foam which was crystallized from a hexanetoluene mixture to gave the sulfoxide of the starting ester, mp 114°–115° (dec.).

Step 2: A solution containing 118 mg of the methyl ester from Step 1 in a mixture of 2 mL tetrahydrofuran and 1 mL of methanol was treated with 1 mL of 2 N LiOH and refluxed for 4 h. The resultant yellow solution was cooled to room temperature, acidified with 1 N HCl and diluted with ethyl acetate. The organic layer was dried over MgSO$_4$. Filtration and concentration, followed by recrystallization from hexane-ethyl acetate gave the title product, mp 142°–144° (dec.).

EXAMPLE 21

1-(p Chlorobenzyl)-α,α-dimethyl-3-phenylsulfonyl-5-(i-propyl)-indole-2-propanoic acid Step 1: To a cold (0°), stirred solution containing 376 mg of methyl 1-(p-chlorobenzyl)-α,α-dimethyl-3-phenylthio-5-(i-propyl)-indole-2-propanoate, from Example 19, Step 1, in 7.4 mL dry methylene chloride, under nitrogen, was added 319 mg of m chloroperbenzoic acid. After 20 min at 0° and 40 min at room temperature the resultant slurry was diluted with ether and washed with saturated aqueous sodium bicarbonate (2×) and brine and dried over MgSO$_4$. Filtration and concentration gave a yellow solid which was recrystallized from a mixture of hexane-toluene to give the sulfone of the starting ester, mp 153°–153.5°.

Step 2: A solution containing 139 mg of the methyl ester from Step 1 in a mixture of 1.5 mL tetrahydrofuran and mL methanol was added 1.0 mL of 2 N LiOH and refluxed for 4 h. The resultant solution was cooled to room temperature, acidified with 1 N HCl and diluted with ethyl acetate. The organic layer was dried over MgSO$_4$, filtered and concentrated to give the title compound as a pale yellow solid which was recrystallized from hexane-ethyl acetate to give the title compound, mp 169°–172°.

EXAMPLE 22

1-(p-Chlorobenzyl)-α,α-dimethyl-5-phenyl-3-phenylthioindole-2-propanoic acid

Following the procedure of Example 10, but using 1-(p-chlorobenzyl)-1-(4-biphenyl)hydrazine hydrochloride and methyl 2,2-dimethyl-4-oxo-5-phenylthiopentanoate as starting materials and hydrolysis at reflux, the title compound was prepared, mp 182°–183°.

Analysis calculated for $C_{32}H_{28}ClNO_2S$: C, 73.06; H, 5.36; N, 2.66; Found: C, 72.58; H, 5.67; N, 2.66.

EXAMPLE 23

1-(p Chlorobenzyl)-α,α-dimethyl-5-fluoro-3-methylthioindole-2-propanoic acid

Following the procedure of Example 10, but using 1-(p-chlorobenzyl)-1-(4-fluorophenyl)hydrazine hydrochloride and methyl-2,2-dimethyl-5-methylthio-4-oxopentanoate as starting materials and hydrolysis at reflux, the title compound was prepared, mp 161°–163°.

EXAMPLE 24

1(p-Chlorobenzyl)-α,α-dimethyl-3-methylthio-5-(isopropyl)-indole-2-propanoic acid Following the procedure of Example 10, but using 1-(p-chlorobenzyl)-1-[4-(i-propyl)phenyl]hydrazine hydrochloride and methyl 2,2-dimethyl-5-methylthio-4-oxopentanoate as starting materials and hydrolysis at reflux, the title compound was prepared, mp 143°–144°.

Analysis calculated for $C_{24}H_{28}ClO_3NS$: C, 67.04; H, 6.65; Found: C, 66.72; H, 6.78.

EXAMPLE 25

1-(p Chlorobenzyl)-3-(t-butylthio)-α,α-dimethyl-5-(i-propyl)-indole-2-propanoic acid Following the procedure of Example 10, but using 1-(p-chlorobenzyl)-1[-(4-(i-propyl)phenyl]hydrazine hydrochloride and methyl 2,2-dimethyl-5-(t-butylthio)-4-oxopentanoate as starting materials and hydrolysis at reflux, the title compound was prepared, mp 189°–192°.

Analysis calculated for $C_{27}H_{34}ClNO_2S$: C, 68.69; H, 7.25; N, 2.97; Found: C, 68.34; H, 7.35; N, 3.08.

EXAMPLE 26

1-(p Chlorobenzyl)-3-(t-butylsulfinyl)-α,α-dimethyl-5-(i-propyl)-indole-2-procanoic acid Following the procedure of Example 20, but using methyl 1-(p-chlorobenzyl)-3-(t-butylthio)-α,α-dimethyl-5-(i-propyl)-indole-2-propanoate (Example 25, Step 1) as the starting material, the title compound was prepared, mp 138°–150° (dec.).

EXAMPLE 27

1-(p-Chlorobenzyl)-3-(t-butylsulfonyl)-α,α-dimethyl-5-(i-propyl)-indole-2-propanoic acid Following the procedure of Example 21, but using methyl 1-(p-chlorobenzyl)-3-(t-butylthio)-α,α-dimethyl-5 (i-propyl)-indole-2-propanoate (Example 25, Step 1) as the starting material, the title compound was prepared, mp 225°–226° (dec.).

EXAMPLE 28

1-(p-Chlorobenzyl)-3-(t-butylthio)-α,α-dimethyl-5-phenylindole-2-propanoic acid

Following the procedure of Example 10, but using 1-(p-chlorobenzyl)-1-(4-biphenyl)hydrazine hydrochloride and methyl 2,2-dimethyl-5-(t-butylthio)-4-oxopentonoate as starting materials and hydrolysis at reflux, the title compound was prepared, mp 245°–246°.

Analysis calculated for $C_{30}H_{32}ClNO_2S$: C, 71.20; H, 6.37; N, 2.76; S, 6.33; Found: C, 71.28; H, 6.35; N, 2.77; S, 6.71.

EXAMPLE 29

1-(p-Chlorobenzyl)-α,α-dimethyl-3-(phenylthio)-5-(i-propyl)-indole-2-butanoic acid Following the procedure of Example 10, but using 1-(p-chlorobenzyl)-1-[4-(i-propyl)phenyl]hydrazine hydrochloride and methyl 2,2-dimethyl-5-oxo-6-phenylthiohexanoate as the starting materials and hydrolysis at reflux, the title compound was prepared, mp 164°–166°.

EXAMPLE 34

3-[1-(p-Chlorobenzyl)-3-(t-butylthio)-5-(i-propyl)-indole-2-yl]-2,2-dimethylpropanol To a solution of 200 mg of methyl 1-(p-chlorobenzyl)-3-(t-butylthio)-α,α-dimethyl-5-(i-propyl)-indole-2-propanoate (from Example 25) in 1.5 mL tetrahydrofuran (THF) was added 0.4 ml of a solution of lithium aluminum hydride (1.0 M in THF) at 0° C. After 2h at 0° C., the reaction mixture was quenched with saturated aqueous Na$_2$SO$_4$, diluted with ether and stirred at room temperature for 1 h. The resultant slurry was filtered and the filtrate concentrated to dryness. The resultant oil was purified by flash chromatography (eluant: hexane-ethyl acetate, 8:2) to give the title compound as a viscous oil. $^1$H NMR (250 MHz, Acetone D) δ: 0.94 (s, 9H), 1.26 (s, 6H), 1.27 (d, 2H J=7.0 Hz), 2.95–3.08 (m, 2H), 2.99 (septuplet, 1H, J=7.0 Hz), 3.27 (d, 2H, J=7.0 Hz), 4.02 (t, 1H, J=7.0 Hz, exchanges with D20), 4.69 (broad s, 2H), 6.92 (d, 2H, J=8.5 Hz), 7.00 (dd, 1H, J=7.5 and 2.0 Hz), 7.24 (d, 1H, J=7.5 Hz); 7.29 (d, 2H, J=8.5 Hz), 7.58 (d, 1H, J=2.0 Hz) IR (CDCl$_3$) 3420 cm$^{-1}$.

EXAMPLE 102

1-(p-Chlorobenzyl)-α,α-dimethyl-5-isopropyl-3-(n-butylthio)indole-2-propanoic acid Following the procedure of Example 104, but using 1-(p-chlorobenzyl)-1-[4-(i-propyl)phenyl]hydrazine hydrochloride and methyl 2,2-dimethyl-4-oxo-5-n-butylthiopentanoate as starting materials followed by hydrolysis at reflux gave the title compound, m.p. 129°–130°.

EXAMPLE 104

1-(p-Chlorobenzyl)-α,α-dimethyl-5-isopropyl-3-cyclohexylthioindole-2-propanoic acid To a mixture of 461 mg of 1-(p-chlorobenzyl)-1-[4-(i-propyl)phenyl]hydrazine hydrochloride and 121 mg of anhydrous sodium acetate in 2.5 mL of anhydrous toluene was added 1.24 mL of glacial acetic acid. After 15 min, a solution containing 336 mg of methyl 2,2-dimethyl-4-oxo-5-cyclohexylthio-pentanoate in 0.5 mL of toluene was added and the reaction mixture stirred for 24h at room temperature. The reaction was then diluted with ether, washed with 1N NaOH(2×), H$_2$O and brine and dried over MgSO$_4$. Filtration and concentration gave a viscous oil which was purified by flash chromatography on silica gel (eluant: hexane-ethyl acetate, 85:15). Hydrolysis to the title compound was effected using 2N LiOH in methanol/THF (1:2) for 6 h at reflux followed by quenching with 1N HCl and filtration, m.p. 166°–168°.

EXAMPLE 107

N-[1-(p-chlorobenzyl)-α,α-dimethyl-5-isopropyl3-t-butylthioindole-2-propanoyl]glycine sodium salt To 472 mg 1-(p-chlorobenzyl)-α,α-dimethyl-5-isopropyl-3-t-butylindole-2-propanoic acid suspended in 5 ml methylene chloride, under nitrogen, was added 417 μL Et$_3$N. 150 μL isobutyl chloroformate was added dropwise. The reaction was cooled to 0° and kept for 1.5h. Glycine ethyl ester hydrochloride (182 mg) dissolved in 1.5 ml methylene chloride was added and the reaction allowed to come to room temperature for 2h. The product was separated by chromatography on silica gel using ethyl acetate-hexane as eluent (3:7). Hydrolysis to the title compound was effected using 1N NaOH in methanol/THF (1:1) for 16h. followed by evaporation of the solvents, m.p. 280°. decomposition.

EXAMPLE 108

1-(p-chlorobenzyl)-α,α-dimethyl-5-isopropyl-3-cyclopropylmethylthioindole-2-propanoic acid Following the procedure of Example 104, but using 1-(p-chlorobenzyl)-1-[4-(i-propyl)phenyl]hydrazine hydrochloride and methyl 2,2-dimethyl-4-oxo-5-cyclopropylmethylthiopentanoate as starting materials followed by hydrolysis at reflux, the title compound was isolated, m.p. 123°–124°.

EXAMPLE 113

1-(p-chlorobenzyl)-α,α-dimethyl-5-isopropyl3-cyclopropylmethylthioindole-2-propionamide To a solution of 110 mg of methyl 1-(p-chlorobenzyl) α,α- dimethyl-5-isopropyl-3-cyclopropylmethylthioindole-2-propanoate (from Example 108) in 1 ml CH$_2$Cl$_2$ was added 1 ml of aminodimethylalane (Me$_2$AlNH$_2$) in hexane/CH$_2$Cl$_2$ (1.0M) and the reaction heated at 65° for 16h. The reaction was quenched with 2N HCl at 0° C., 0.5M NaK tartrate was added and the solution extracted with ether. The product from ether was purified by chromatography on silica gel (Toluene/Acetone/Acetic acid) 85:15:1 to yield the title compound, m.p. 137°–138°.

EXAMPLE 115

1-(p-aminobenzyl)-α,α-dimethyl-5-isopropyl-3-phenylsulfonylindole-2-propanoic acid Step 1: Methyl [1-(4-nitrobenzyl)-α,α-dimethyl-5-isopropyl-3-phenylsulfonylindole]-2-propanoate was prepared according to the method described in Example 22, but using 1-(p-nitrobenzyl) 1-[4-(i-propyl)phenyl]hydrazine hydrochloride and methyl 2,2-dimethyl-4-oxo-5-phenylthiopentanoate as starting materials.

Step 2: A solution of 480 mg methyl[1-(4-nitrophenyl)-α,α-dimethyl-5-isopropyl-3-phenylsulfonylindole-2-propanoate] in 45 ml ethyl acetate was heated with 100 mg Pd/C (5%) catalyst and the solution hydrogenated a 45 psi for 16h. A further 50 mg catalyst was added and the hydrogenation continued for another 16h. The catalyst was removed by filtration through celite and the product isolated (480 mg) after removal of solvent. Hydrolysis was achieved by treatment of the ester with 2N NaOH in 3 ml MeOH/THF 1:1. The solution was neutralized with 0.5N HCl and the product extracted with ethyl acetate 3×10 ml. The solution was dried (Na$_2$SO$_4$) and stripped to yield the title product, m.p. 290° decomposition.

EXAMPLE 116

1-(p-Chlorobenzyl)-α,α-dimethyl-5-isopropyl3-(5-chlorobenzothiazol-2-ylthio)indole-2-propanoic acid Following the procedure of Example 104, but 1-(p-chlorobenzyl)-1-[4-(i-propyl)phenyl]-hydrazine hydrochloride and methyl 2,2-dimethyl-4-oxo-5-(5-chlorobenzothiazol-2-ylthio)pentanoate as starting materials followed by hydrolysis at reflux gave the title compound, m.p 154°–156°.

EXAMPLE 124

1-[(p Chlorobenzyl)-5-(isopropyl)-3-(t-butylthio)-indole-2-methyl]-1-cyclopentane carboxylic acid Following the procedure of Example 104, but using 1-(p-chlorobenzyl)-1-[4-(i-propyl)phenyl]-hydrazine hydrochloride and methyl 1-[3-(t-butylthio)-2-oxoprop-1-yl]cyclopentane carboxylate as starting materials followed by hydrolysis at reflux gave the title compound, m.p. 203°–204°.

EXAMPLE 127

1-(P-Chlorobenzyl) α,α-dimethyl-5-isopropyl-3-(1-buten-4-ylthio)indole-2-propanoic acid, sodium salt Following the procedure of Example 104, but using 1-(p-chlorobenzyl)-1-[4-(i-propyl)phenyl]-hydrazine hydrochloride and methyl 2,2-dimethyl-4-oxo-5-(1-buten-4-ylthio)pentanoate as starting materials followed by hydrolysis at reflux and isolation as the sodium salt, the title compound was prepared, m.p. 206°–207°.

EXAMPLE 128

1-(p-Chlorobenzyl)-α,α-dimethyl-5-isopropyl-3-(benzylthio)indole-2-propanoic acid Following the procedure of Example 104, but using 1-(p-chlorobenzyl)-1-[4-(i-propyl)phenyl]-hydrazine hydrochloride and methyl 2,2-dimethyl-4-oxo-5-benzylthiopentanoate as starting materials followed by hydrolysis at reflux gave the title compound, m.p. 135°–137°.

EXAMPLE 129

1-(p Chlorobenzyl)-α,α-dimethyl-5-isopropyl-3-(2-isopropylphenylthio)indole-2-propanoic acid Following the procedure of Example 104, but using 1-(p-chlorobenzyl)-1-[4-(i-propyl)phenyl]-hydrazine hydrochloride and methyl 2,2-dimethyl-4-oxo-5-(2-isopropylphenylthio)pentanoate as starting materials followed by hydrolysis at reflux gave the title compound, m.p. 142°–143°.

EXAMPLE 130

1-(p-chlorobenzyl)-α,α-dimethyl-5-isopropyl-3-(2-isopropylphenyl-sulfonyl)indole-2-propanoic acid Following the procedure of Example 21, but using methyl 1-(p-chlorobenzyl)-α,α-dimethyl-5-isopropyl-3-(2-isopropylphenylthio)-indole-2-propanoate as starting material (from Example 129) followed by hydrolysis at reflux gave the title compound, m.p. 181°–182°.

EXAMPLE 131

1-(p-Chlorobenzyl)-3-(t-butylthio)-α,α-dimethyl-5-(i-propyl)indole-2-propanoic acid, sodium salt Step 1: A 1L flask equipped with a magnetic stirrer and a nitrogen inlet was charged with 1-(p-chlorobenzyl)-1-[4-(i-propyl)phenyl]hydrazine hydrochloride (62 g, 0.2 mole), anhydrous sodium acetate (18q, 0.22 mol) and toluene (400 mL). Glacial acetic acid (200 mL) was added, the mixture stirred for 15 min and then treated with a solution of methyl 5-(t-butylthio)-2,2-dimethyl-4-oxopentanoate (54.1 q, 0.22 mol) in toluene (100 mL). The resultant mixture was stirred in the dark for 4 days.

The reaction mixture was diluted (4×) with 200 mL of distilled water and the phases separated. The aqueous phase (pH≈2) was discarded and the organic phase neutralized by shaking with NaOH (5N). The organic layer was separated and evaporated without drying to give a brown syrup which was hydrolyzed without further purification.

Step 2: The resulting syrup obtained in step 1 was dissolved in 300 mL of MeOH and 100 mL of THF and then 100 mL of 2N LiOH was added. The resulting suspension was stirred at reflux overnight. The clear mixture was allowed to cool to room temperature and neutralized with HCl (3N). The reaction was set aside in an ice bath and the product crystallized out. The crude acid was then isolated by filtration and resuspended in 400 mL of cold methanol and swished for 3–4 hours. The product was then filtered from the swished liquors and was dried in vacuo to give 55 q of the title compound as the free acid. A second crop of 7 q was obtained from the mother liquors.

Step 3: To a solution of the acid isolated in step 3 (36.5 gm, 0.077 mol) in distilled tetrahydrofuran (234 ml), was added a 1.00 M solution of sodium hydroxide in deionized water (76 ml). The reaction mixture was stirred at room temperature for 30 min and then concentrated to a viscous oil from which was evaporated ethanol (2×) and ether (2×). Crystallization of the residue from hexane and washing with ether gave after drying (50° C., 0.5 Torr) the title compound, m.p. 289° C. (dec).

What is claimed is:

1. A compound of the formula:

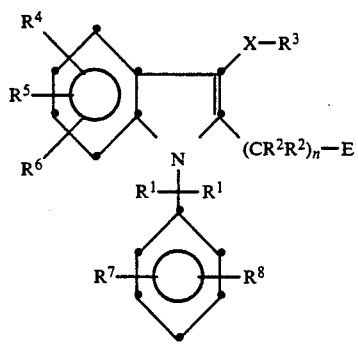

wherein:

$R^1$ is H or loweralkyl;

$R^2$ is H or loweralkyl, or two $R^2$'s may be joined to form a ring of 3–6 atoms;

$R^3$ is —$(CH_2)_m$—Het;

$R^4$, $R^5$ and $R^6$ is each independently H, lower-alkyl, $C_2$-$C_6$ alkenyl, or —$(CR^2R^2)_pM$;

$R^7$ and $R^8$ are independently H, $C_1$-$C_3$ alkyl, halogen, OH, CN, $CF_3$, $C_1$-$C_3$ alkoxy, $C_1$-$C_3$ alkylthio, $CO_2H$, $C_1$-$C_3$ alkoxycarbonyl, $C_1$-$C_3$ alkylcarbonyl, or azide;

$R^9$ is $CF_3$, loweralkyl, substituted or unsubstituted benzyl, or substituted or unsubstituted phenyl;

$R^{10}$ is H, loweralkyl, unsubstituted phenyl, unsubstituted benzyl, or two $R^{10}$'s attached to a nitrogen may form a ring of 5 to 7 members;

$R^{11}$ is H or —$(CH_2)_qR^9$;

$R^{12}$ is loweralkyl, substituted or unsubstituted benzyl, or substituted or unsubstituted phenyl;

$R^{13}$ is H, loweralkyl, substituted or unsubstituted phenyl, or substituted or unsubstituted benzyl;

$R^{14}$ is —$CH_2CH_2N(R^{10})_2$, $CH_2CH(OH)CH_2OH$, —$CH_2O_2CC(CH_3)_3$, —$CH(CH_3)O_2CC(CH_3)_3$,

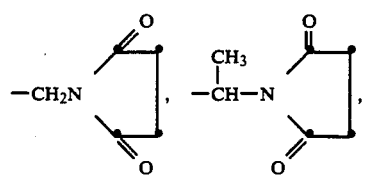

-continued

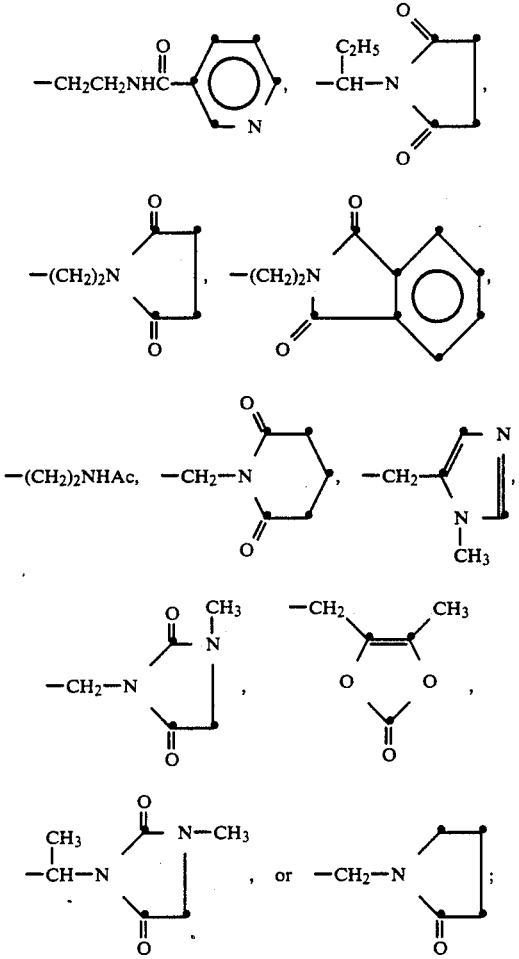

E is CH₂OH, CO₂R¹³, CO₂R¹⁴, tetrazol-5-yl, CHO, C(O)NR²R², C(O)NHS(O)₂R⁹, or C(O)N-(OR²)R²;

M is a) OR¹⁰;
b) halogen;
c) CF₃;
d) SR⁹;
e) substituted or unsubstituted phenyl;
f) COOR¹⁰;

g) $\overset{O}{\underset{}{C}}-R^{11}$;

h) tetrazole;

i) $-NH-\overset{O}{\underset{}{C}}-R^{11}$;

j) —NR¹⁰R¹⁰;
k) —NHSO₂R⁹;

l) $-\overset{O}{\underset{}{C}}-CH_2OH$;

m) —S(O)R⁹;
n) —CONR¹⁰R¹⁰;
o) —S(O)₂NR¹⁰R¹⁰;

p) —S(O)₂R⁹;
q) NO₂;

r) $O-\overset{O}{\underset{}{C}}-R^{11}$;

s) $O-\overset{O}{\underset{}{C}}-NR^{10}R^{10}$;

t) $O-\overset{O}{\underset{}{C}}-OR^{12}$;

u) CN;
v) N₃; or
w) H;

X is O, S, S(O), or S(O)₂;
m is 0–2;
n is 0–5;
p is 0–3;
q is 0–4;

substituted phenyl and substituted benzyl mean 1 or 2 substituents on the benzene ring selected from C₁-C₃ alkyl, halogen, CN, CF₃, C₁-C₃ alkoxy, C₁-C₃ alkylthio, CO₂H, C₁-C₃ alkoxycarbonyl, C₁-C₃ alkylcarbonyl, and azide;

Het is 2-, 3-, or 4-pyridyl; or 2-, 3- or 4-quinolinyl, each optionally substituted with 1 or 2 substituents selected from C₁-C₃ alkyl, halogen, CN, CF₃, C₁-C₃ alkoxy, C₁-C₃ alkylthio, CO₂H, C₁-C₃ alkoxycarbonyl, C₁-C₃ alkylcarbonyl, and azide;

and the pharmaceutically acceptable salts thereof.

2. A compound of claim 1 of the formula:

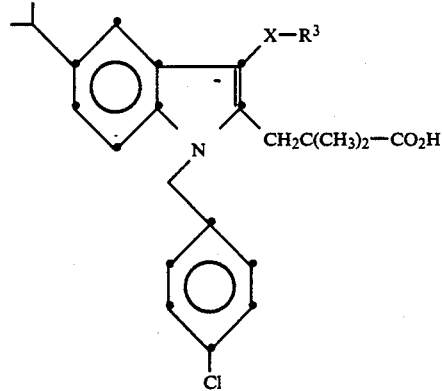

wherein the substituents are as follows:

| Ex. | R³ | X |
|---|---|---|
| 64. | 4-pyridyl | S |
| 65. | 2-pyridyl | S |
| 68. | CH₂-2-pyridyl | S |
| 69. | CH₂-4-pyridyl | S |
| 121. | 2-quinolinyl | S |

3. A pharmaceutical composition comprising a therapeutically effective amount of a compound of claim 1 and a pharmaceutically acceptable carrier.

4. A method of preventing the synthesis of leukotrienes in a mammal which comprises administering to said mammal an effective amount of a compound of claim 1.

5. The method of claim 4 wherein the mammal is man.

6. A method of inducing cytoprotecting in a mammal comprising administering to a mammal in need of such treatment a cytoprotective amount of a compound of claim 1.

7. A method of treating inflammatory diseases of the eye in a mammal which comprises administering to a mammal in need of such treatment a therapeutically effective amount of a compound of claim 1.

8. The method of claim 7 wherein the mammal is man.

* * * * *